(12) United States Patent
Taton et al.

(10) Patent No.: US 7,807,750 B2
(45) Date of Patent: Oct. 5, 2010

(54) THERMALLY-REACTIVE POLYMERS

(75) Inventors: Kristin S. Taton, Little Canada, MN (US); Patrick E. Guire, Eden Prairie, MN (US)

(73) Assignee: SurModics, Inc., Eden Prairie, MN (US)

( * ) Notice: Subject to any disclaimer, the term of this patent is extended or adjusted under 35 U.S.C. 154(b) by 210 days.

(21) Appl. No.: 10/944,384

(22) Filed: Sep. 17, 2004

(65) Prior Publication Data

US 2006/0030669 A1    Feb. 9, 2006

Related U.S. Application Data

(60) Provisional application No. 60/599,683, filed on Aug. 6, 2004.

(51) Int. Cl.
    *C08F 279/02*    (2006.01)
    *C08F 251/00*    (2006.01)
    *C08F 253/00*    (2006.01)
    *C08F 255/00*    (2006.01)
    *C08F 261/00*    (2006.01)
    *C08F 297/00*    (2006.01)

(52) U.S. Cl. ................ 525/69; 525/263; 525/273; 525/326.9; 525/387

(58) Field of Classification Search ............ 525/387, 525/69, 263, 273, 326.9
See application file for complete search history.

(56) References Cited

U.S. PATENT DOCUMENTS

| | | | |
|---|---|---|---|
| 3,949,018 A | 4/1976 | Agouri et al. | |
| 4,851,459 A | 7/1989 | Ramalingam | |
| 5,011,981 A | 4/1991 | Tsuboniwa et al. | |
| 5,552,224 A | 9/1996 | Laughner et al. | |
| 5,760,149 A | 6/1998 | Sanchez et al. | |
| 6,096,369 A | 8/2000 | Anders et al. | |
| 6,127,448 A * | 10/2000 | Domb ................ | 523/105 |
| 6,156,345 A | 12/2000 | Chudzik et al. | |
| 6,368,587 B1 | 4/2002 | Anders et al. | |

FOREIGN PATENT DOCUMENTS

| | | |
|---|---|---|
| DE | 4344516 | 6/1995 |
| EP | 0294237 | 6/1988 |
| EP | 0321292 | 12/1988 |
| EP | 0887369 | 12/1998 |
| EP | 0893165 | 1/1999 |
| GB | 1408412 | 10/1975 |
| JP | 07207064 | 8/1995 |
| JP | 11217451 | 8/1999 |
| JP | 2004162203 | 6/2004 |
| WO | WO 95/18161 | 7/1995 |

* cited by examiner

*Primary Examiner*—Nathan M Nutter
(74) *Attorney, Agent, or Firm*—Kagan Binder, PLLC

(57) ABSTRACT

A thermally-reactive polymer that forms a polymer-coupled reactive species upon heating is described and useful for forming coated surfaces. The polymer-coated surface has improved lubricity and passivity. A thermally-reactive quaternary amine-containing polymer was produced that provides passivity and anti-microbial activity.

41 Claims, No Drawings

THERMALLY-REACTIVE POLYMERS

The present non-provisional Patent Application claims the benefit of priority under 35 USC 119 from commonly owned United States Provisional Patent Application having Ser. No. 60/599,683, filed on Aug. 6, 2004, titled THERMALLY-REACTIVE POLYMERS, which Patent Application is incorporated herein by reference in its entirety.

FIELD OF THE INVENTION

This invention relates to polymers having thermally-reactive groups, and substrates having a coating that includes these polymers. More specifically, the invention relates to polymers having a thermally-reactive group which is pendent from the polymer backbone and that can be activated to form a coating on the substrate.

BACKGROUND

Medical devices have become increasingly complex in terms of function and geometry. More recently, it has been recognized that chemical coatings provided to the surface of medical devices can enhance function and effectiveness of the medical device in vivo. In particular, there has been a great need for providing coatings to small implantable medical devices, such as stents, which often have intricate geometries. In some cases, when these medical devices having intricate geometries are subject to a coating procedure, webbing or bridging of the coating solution may occur, resulting in a coating that hinders the device from functioning properly. Other coating reagents and techniques utilize light to fix the coating compound on the device surface. However, methods involving light activation can potentially be inadequate for providing uniform coatings over the entire surface of the device. In particular inner surfaces of devices can be difficult to access with an activating amount of light.

It is therefore desirable to provide uniform coatings to devices having intricate geometries and coatings to portions of the device that have inner surfaces.

It can be advantageous to provide coatings that improve the biocompatibility and improve surface properties, such as lubriciousness, of the coated device.

SUMMARY

The present invention provides polymers having thermally-reactive groups, herein referred to as "thermally-reactive polymers," which can be utilized for a number of purposes including forming polymeric coatings on the surface of articles. Use of the thermally-reactive polymer of the invention can provide advantages in many applications wherein use of a polymer is desired, particularly uses wherein polymeric coatings are provided to impart one or more desirable properties to all or a portion of the surface of an article. For example, and as shown herein, the thermally-reactive polymers can be used to improve the surface properties of devices that come in contact with biological factors, such as body fluids and tissue, or microorganisms. The present invention demonstrates that the thermally-reactive polymers can be used to provide one or more beneficial properties such as improved lubricity, improved passivity against protein adsorption, and antimicrobial activity.

A profound advantageous aspect of the invention is the ability to provide a polymeric coating to portions of an article that may be otherwise difficult to coat using non-thermal methods. In many cases, it is desirable to provide surface coatings to articles that have complex surface geometries, for example, small medical devices, such as stents. With these and other devices a coating may be necessary to ensure that the device functions properly. If portions of the device are impeded with biological debris such as protein and cells, the device may loose its effectiveness. However, according to the present invention a polymeric coating is able to be formed on these types of surfaces using heat to form a coated layer.

According to the invention the polymeric coating can be applied to desired surfaces of an article by disposing the thermally-reactive polymer on the article and then heating the article to activate the thermally-reactive groups of the polymer. In traditional methods for preparing a coating, it may be difficult to provide other sources of activation energy, such as light, to inner surfaces of articles. However, according to the invention, the thermally-reactive polymer is able to form covalent bonds upon heating, which results in the association of the thermally-reactive polymer with the surface of the article and formation of a coated layer. Covalent bonding can promote the association of the polymer in a number of ways, including direct covalent bonding to the surface, and/or covalent boding to other components in the coated layer. In one aspect of the invention the article has one or more surfaces that are inaccessible to, or obstructed from receiving light irradiation. For example, the article can have surfaces, wherein the surfaces are not able to receive sufficient amounts of light irradiation for coupling the coating to those surfaces.

The use of heat to promote formation of a coated layer is particularly advantageous because the device can be uniformly subject to the same, or approximately the same, amount of heat (activation energy) over all surfaces on which a coating having the thermally-reactive polymer has been deposited. This can promote the formation of a coated layer over the surfaces that are uniform in one or more aspects. For example, in one aspect a coating having a uniform thickness over all coated areas of the device can be achieved using the reagents and methods of the current invention.

The use of a thermally-reactive polymer can also be advantageous when it is desired to include a bioactive agent, such as a pharmaceutical or drug, in the coating. In many cases bioactive agents are sensitive to other forms of activating sources such as chemicals and irradiation. However, the thermally-reactive polymers, which include thermally-reactive groups that have low activation energies, can be used to form a coating that includes a bioactive agent without compromising the activity (e.g., stability) of the agent. This means that the bioactive agent is subject to minimal heating requirements during the process of forming the coating. In this case, use of the thermally activatable polymers provides a particularly advantageous route for the preparation of drug delivery surfaces.

Furthermore, use of the thermally-reactive polymers is also advantageous since the methods for preparing a coating can be efficient and inexpensive. In some aspects, a coated layer can be prepared in a minimal number of steps, which can be performed relatively quickly. Furthermore, simple, inexpensive apparatus can be used to heat the article in order to promote formation of a coated layer.

According to the invention, a thermally-reactive polymer is provided. The polymer includes the features of a backbone having thermally-stable linkages and one or more thermally-reactive group(s), which are pendent from the polymer backbone. Upon application of heat the thermally-reactive group on the polymer becomes activated, which can react with and form a covalent bond with another moiety. The one or more thermally-reactive group(s) are arranged to allow the polymer to form a coated layer on a surface of an article. For example, a coated layer can be formed by the thermally-reactive group covalently bonding to the surface of the substrate on which it is deposited, or a coated layer can be formed by the thermally-reactive group covalently bonding to another component that is deposited along with the thermally reactive polymer on the surface.

The thermally-reactive group, which can be present at one or more positions along the length of the polymeric backbone, can be selected from chemical groups that, upon heating: (a) generate carbenes and nitrenes, (b) homolytically cleave resulting in the generation of two different radical species, (c) provide reactive triplet states, and (d) provide radical anions and radical cations. In some aspects the thermally-reactive polymer includes 10 molar percent or more thermally-reactive groups.

In one preferred aspect of the invention, the thermally-reactive group homolytically cleaves upon heating, resulting in the generation of two different radical species. When this type of thermally-reactive group is pendent from the polymer, the thermally-reactive polymer can decompose into a polymer coupled radical species and a second radical species. In forming a coated layer the second radical species reacts with another moiety, such as the surface or another polymer, to cause abstraction of a hydrogen atom from the moiety, promoting formation of radical species on the moiety. This radical species on the moiety can then react with the polymer-coupled radical species to covalently bond the polymer to the moiety. Examples of this type of thermally-reactive group include peroxide and peroxyester groups.

In most cases the backbone of the thermally-reactive polymer consists essentially of thermally-stable linkages. However, in other cases thermally-reactive groups can be present in the backbone of the polymer, which can be treated with heat to promote the breakdown into smaller thermally-reactive polymers, which can also be used to form a coating.

The backbone of the thermally-reactive polymer can be obtained or prepared to provide a polymeric coating with desired properties. In one aspect, the thermally-reactive polymer has properties that allow for the formation of a hydrophilic coating, such as a hydrogel, or a coating that has hydrogel-like qualities. In some aspects the polymer backbone can be selected from the group consisting of homopolymers and copolymers of polyester, polycarbonate, polyamide, polyether, polysulfone, polyurethane, polyimide, and polyvinyl backbones. In some aspects the polymer backbone is formed from monomers having ethylenically unsaturated groups. Some particularly preferred polymers formed from monomers having ethylenically unsaturated groups are polyvinyl polymers which include poly(meth)acrylamides, polyacrylamides, and poly(vinylpyrrolidone).

In other aspects of the invention the thermally-reactive polymer has a Mw of 1000 or greater.

In other aspect, the invention provides an article, such as a medical device, that has a coated layer that includes a thermally-reacted polymer. In the coated layer, the thermally reacted group is covalently bonded to another moiety, the covalent bonding allowing the formation of a coated layer on the surface. In some aspects, the coated layer is formed wherein an atom a hydrogen atom of the other moiety has been abstracted by reaction with the second radical species and forms a covalent bond between the other moiety and the polymer coupled radical species. In some aspects the other moiety is the surface and the polymer is covalently bound to the surface via the thermally-reacted group.

In other aspects, the other moiety is a polymer (for example, a secondary polymer) that is different than the thermally reactive polymer present in the coating. The secondary polymer can be, for example, another thermally reacted polymer or a polymer that does not include thermally-reactive(d) groups. In this aspect a covalent bond exists between the secondary polymer and the polymer having the thermally-reacted group, the bond being formed by the thermally-reacted group.

The coating on the article can include one, or more than one, coated layer. If the coated article has more than one coated layer, the layers can be the same or different. For example, one coated layer can include components including the thermally-reacted polymer and another layer can include the same or different components.

The invention also provides methods for forming a coated layer on an article, wherein the coated layer is formed using the thermally-reactive polymer. According to the method, an article (such as a medical device) is obtained. The thermally-reactive polymer, which can be present in a coating composition, is deposited on all, or a portion of the surface of the device. By heating the thermally-reactive polymer, a coated layer is formed on the surface of the article. The thermally-reactive polymer can be heated and decompose into products that include a polymer-coupled radical species. In some embodiments the step of heating produces a second radical species and a polymer-coupled radical species, wherein the polymer-coupled radical species becomes associated with the surface of the article by covalent bonding to the surface or to another moiety. In most cases the thermally-reactive groups can be activated by heating the thermally-reactive polymer at temperature(s) of 110° C. or less, however, higher temperatures can be used depending on, for example, the type of thermally reactive group(s) pendent from the polymer, the substrate, and other components that can be present in the coating composition. The method can be performed with or without additional coating steps. In some aspects the thermally-reactive polymer can be dried on the surface of the article prior to or during the step of heating.

The invention also provides methods for improving the lubricity of a surface of an article. The method includes (a) obtaining a polymer comprising (i) a backbone comprising thermally-stable linkages and (ii) a thermally-reactive group; (b) disposing the polymer on the surface; and (c) heating the polymer to form a coated layer on the surface of the article. The coated layer formed from the method has a water contact angle that is reduced relative to an uncoated article by an amount in the range of about 25° to about 60°. In preferred aspects, it has been found that the coated surface maintains the reduced water contact angle measurement following physical challenge, meaning that implantable devices that have a coated layer that includes the thermally-reacted polymer could maintain a lubricious surface after being subject to abrasive conditions within the body.

The invention also provides methods for passivating against protein adsorption on a surface. The method includes (a) obtaining a polymer comprising (i) a backbone comprising thermally-stable linkages and (ii) a thermally-reactive group; (b) disposing the polymer on the surface; and (c) heating the polymer to form a coated layer on the surface of the article. The method allows protein adsorption to be reduced by 35% or more on the polymer-coated surface as compared to an uncoated surface.

The invention further provides methods for impeding bacterial growth near or on a surface of an article. The method includes (a) obtaining a polymer comprising (i) a backbone comprising thermally-stable linkages, (ii) a quaternary amine group, and (iii) a thermally-reactive group; (b) disposing the polymer on the surface; and (c) heating the polymer to form a coated layer on the surface of the article. The coated surface demonstrates reduced bacterial adherence and/or colonization as compared to an uncoated control.

The invention also provides thermally-reactive polymers having quaternary amine groups that can be useful for impeding bacterial growth near or on a surface of an article. In some aspects the thermally-reactive polymer includes 10 molar percent or more quaternary amine groups. In particular, it is particularly useful to utilize polymers having quaternary amine groups in the range of 50 molar percent to 90 molar percent.

DETAILED DESCRIPTION

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The terminology used herein is not intended to limit the scope of the invention. Throughout the text, including the appended claims, the singular forms "a," "an," and "the" include plural reference unless the context clearly dictates otherwise. Thus, for example, a reference to "a reactive group" is a reference to one or more reactive groups and includes equivalents thereof known to those skilled in the art. In this invention, certain terms are used frequently, the meanings of which are provided herein. Unless defined otherwise, terms used herein have the same meaning as commonly understood to one of ordinary skill in the art in this field of technology. Some terms may also be explained in greater detail later in the specification.

"Polymer" refers to a compound having one or more of the same or different repeating monomeric units and includes linear homopolymers and copolymers, branched homopolymers and copolymers, graft homopolymers and copolymers, and the like. Polymers are typically formed by polymerization of monomers having polymerizable groups. A polymer therefore includes monomeric units and has a "polymeric backbone" formed by the "polymeric linkages," which are covalent bonds formed between monomeric units during polymerization.

For purposes of discussion herein, the inventive polymers can be thought of as including at least two basic components: (1) a polymer backbone that includes thermally-stable linkages, and (2) a thermally reactive group pendent from the polymer backbone. Generally, the polymeric backbone provides one or more desired features to a coating. These features can include structural features and/or features which provide properties such as wettability, lubriciousness, anti-adsorptive properties, etc. In turn, the thermally-reactive groups provide a mechanism to associate the coating materials with a substrate to form a coating. It will be apparent upon review of this disclosure that other components can be included with the inventive polymers. Polymers containing at least these two basic components are referred to herein as "thermally-reactive polymers."

The term "thermally-reactive groups" refers to classes of compounds that decompose thermally to form reactive species that can form covalent bonds. Therefore, when referring to decomposition of the thermally-reactive polymer it is the pendent thermally-reactive group that is subject to decomposition. The covalent bonds allow the thermally-reactive polymer to form a coated layer on a surface by, for example, allowing covalent bonding between the polymer and the surface or between the polymer and another component in the coating.

As used herein, "coating" refers to the components, in total, that are deposited on a substrate. The coating includes all of the coated layers that are formed on the surface of the substrate. A "coated layer" is formed by depositing a compound, and more typically a composition that includes one or more compounds suspended, dissolved, or dispersed, in a particular solution.

According to the invention, the thermally-reactive polymers useful for providing a coating to a surface include a) a polymeric backbone comprising thermally-stable linkages and b) a thermally-reactive group, wherein, upon application of heat, the polymer decomposes into products comprising a polymer-coupled reactive species.

In some aspects of the invention, the polymer decomposes into a polymer-coupled radical species and a second radical species. In order for the polymer to become associated with the surface, the thermally-reactive group decomposes to a polymer-coupled radical species that abstracts a hydrogen atom from a target moiety, such as the surface or another component in the coating composition, such as another polymer, thereby forming a target radical species. The target radical species then reacts with the polymer-coupled radical species to covalently bond the polymer to the target moiety. This allows a covalent bond to be formed between the polymer and the surface. In other cases the polymer can react with and covalently bond to another moiety that allows the formation of a coated layer on the surface.

The thermally-reactive polymer includes a backbone comprising thermally-stable linkages and a thermally-reactive group. In some embodiments, a monomeric unit (I), including a thermally-reactive group (of a thermally-reactive polymer), is shown below. $X_2$—R of the monomeric unit represents the thermally-reactive group. $X_1$ represents at least a portion of the monomeric unit that is included in the polymeric backbone. Upon application of heat, the thermally-reactive group decomposes to provide products comprising a polymer-coupled radical species (II) and a second radical species (III).

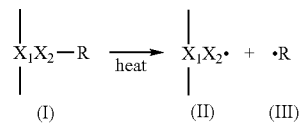

In the least, the thermally-reactive group consists of a pair of atoms having a heat sensitive (labile) bond; exemplary pairs include oxygen-oxygen (peroxide), nitrogen-oxygen, and nitrogen-nitrogen. According to the invention heat at temperatures not more than 200° C., more typically not more than 110° C., and most typically not more than 80° C. causes the decomposition of the thermally-reactive groups of the polymer thus forming species (II) and (III).

Both carbenes and nitrenes possess reactive electron pairs that can undergo a variety of reactions, for example, including carbon bond insertion, migration, hydrogen abstraction, and dimerization. Examples of carbene generators include diazirines and diazo-compounds. Examples of nitrene generators include aryl azides, particularly perfluorinated aryl azides, acyl azides, and triazolium ylides. In addition, groups that upon heating form reactive triplet states, such as dioxetanes, or radical anions and radical cations, pendent from the polymer backbone can be used to form the thermally-reactive group. Generally these compounds thermally decompose at temperatures of not more than 200° C. Any of these thermally-reactive groups, as well as mixtures of these thermally-reactive groups, could be attached to thermally stable polymeric backbones.

In one embodiment the thermally-reactive group of the polymer includes a peroxide —(O—O)— group. A monomeric unit of the thermally-reactive polymer having a peroxide thermally-reactive group is shown by structure (IV):

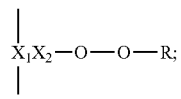
(IV)

wherein $X_1$ is a portion of the polymeric backbone of the polymer, $X_2$ is a group linking the polymer backbone to the peroxide that includes an atom that can form a radical (i.e., the radical portion of polymer coupled radical species) following decomposition of the peroxide group; and R is H or any carbon-containing compound that can form an oxy radical (i.e., the second radical species) following decomposition of the peroxide group. In some aspects, $X_2$, R, and the two oxygen atoms are included in a ring structure pendent from the polymer backbone.

Thermally-reactive polymers having a peroxide group can include other, more specific, thermally-reactive peroxide-containing species. These include, for example, thermally-reactive polymers with a monomeric unit having a thermally-reactive diacyl peroxide group (V):

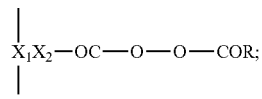
(V)

thermally-reactive polymers with a monomeric unit having a thermally-reactive peroxydicarbonate group (VI):

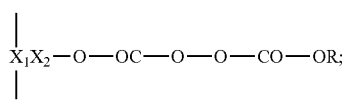
(VI)

thermally-reactive polymers with a monomeric unit having a thermally-reactive dialkylperoxide group (VII):

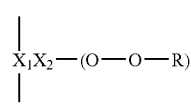
(VII)

wherein both R and $X_2$ are carbon-containing group, such as alkyl; and thermally-reactive polymers with a monomeric unit having a thermally-reactive peroxyester group (VIII):

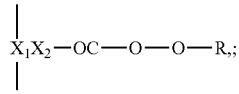
(VIII)

thermally-reactive polymers with a monomeric unit having a thermally-reactive peroxyketal group (IX):

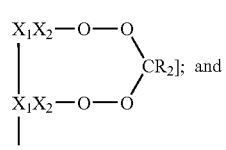
(IX)

thermally-reactive polymers with a monomeric unit having a thermally-reactive dioxetane group (X):

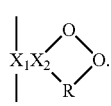
(X)

Dioxetanes are four-membered cyclic peroxides that can be dissociated at even lower temperatures than standard peroxides due to the ring strain of the molecules. Activation energies are typically 5-8 kcal/mole lower than simple peroxides with an average bond dissociation energy of 25 kcal/mole. While the initial step in the decomposition of dioxetanes is cleavage of the O—O bond, the second step breaks the C—C bond creating one carbonyl in the excited triplet state, and one in an excited singlet state. The excited triplet state carbonyl can extract a hydrogen from a target moiety, forming two radical species, one of which is on the target moiety and one of which is on the carbon of the carbonyl with the oxygen becoming hydroxy, thereby forming a new covalent bond between the thermally reactive polymer and the target moiety In a preferred embodiment, thermally-reactive polymers include (a) a backbone comprising thermally-stable linkages and (b) a thermally-reactive peroxyester group. Suitable monomeric units of this polymer are shown by structure VIII.

In some embodiments of the invention it is preferable to prepare and utilize thermally-reactive polymers that have a relatively low activation energy (i.e., temperature of decomposition), for example, in the range of 30-60 kcal/mol. A low activation energy can allow for increased rate of reaction of the polymer-coupled reactive species with the target moiety, thereby generally improving the efficiency and enhancing the rate of the polymer coupling to the target moiety. With lower activation energies, side reactions and disproportionation will be less favored. This process is facilitated by providing a thermally-reactive polymer that can decompose into, for example, a polymer-coupled radical species (II) that is relatively stable.

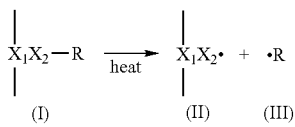

In some embodiments, $X_2$ of formula I, and in more specific embodiments, $X_2$ of compound IV (peroxide thermally-reactive group):

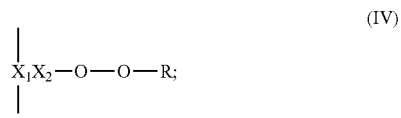

includes a group that provides a stable polymer-coupled radical. Preferred $X_2$ groups that provide a stable radical include, for example, benzyl and diphenylacetyl groups, which can form polymer-coupled benzyl and diphenylacetyl radicals, respectively, upon decomposition of the polymer. The $X_2$ group can also include an oxygen-containing moiety thereby improving the reactivity of the polymer-coupled radical species (II); suitable oxygen-containing moieties include, for example, alkyl groups substituted with hydroxyl or methoxy groups. Other preferred $X_2$ groups include, for example, phenylacetyl, benzoyl, phenylbenzyl, hydrocinnamoyl, mandelyl, phenacyl, phenethyl, thiophenacyl, triphenylmethyl, biphenylacetal, biphenylethyl, and biphenylmethyl. Other $X_2$ groups include allyl, substituted allyl, and carboxyl.

In a preferred embodiment, the thermally-reactive polymer includes a) a backbone comprising thermally-stable linkages and b) a thermally-reactive peroxyester group wherein, upon application of heat, the polymer decomposes into products comprising a polymer-coupled radical species and a second radical species, wherein the polymer-coupled radical species comprises a group selected from benzyl, diphenylacetyl, phenylacetyl, benzoyl, phenylbenzyl, hydrocinnamoyl, mandelyl, phenacyl, phenethyl, thiophenacyl, triphenylmethyl, biphenylacetal, biphenylethyl, biphenylmethyl, allyl, substituted allyl, and alkoxy substituted alkyl.

In some embodiments of the invention it is preferable to prepare and utilize thermally-reactive polymers that provide a highly reactive second radical species upon decomposition of the polymer. These second radicals can promote the formation of surface radical species that then can react with the polymer-coupled radical species to bond the polymer to the surface. In some embodiments the second radical species is an oxy-based radical species such as hydroxy or alkoxy. In one embodiment, the R-group is t-butyl.

The thermally-reactive polymer contains thermally-reactive groups in an amount sufficient to promote the formation of a coated layer that includes the thermally-reacted polymer. The thermally-reactive polymer includes at least one thermally-reactive group and more preferably about 10 molar percent or more thermally-reactive groups. In more preferred embodiments the thermally-reactive polymer includes an amount of thermally-reactive groups in the range of 10-30 molar percent.

"Molar percent" can be calculated by dividing the number of chemical groups, such as thermally-reactive groups or quaternary amine groups, by the number of monomeric units present in the thermally-reactive polymer. For example, a polyacrylamide polymer having 10 molar percent peroxyester groups will have 1 peroxyester group per 10 acrylamide monomeric units of the polymer.

The polymer backbone generally refers to the polymer chain without addition of groups that provide a particular functionality to the polymer, such as thermally-reactive groups or quaternary amine groups, which can be specifically coupled to the polymer backbone. The thermally-reactive polymer includes "thermally-stable linkages", meaning, specifically, that the covalent bonds between the monomeric units of the polymer are not subject to cleavage upon application of an amount of heat that will cause the decomposition of the thermally-reactive groups pendent from the polymer. In some aspects, thermally-stable linkages are stable to temperatures of typically 200° C. or more.

The polymer backbone typically includes carbon and preferably one or more atoms selected from nitrogen, oxygen, and sulfur. Thermally-stable polymer backbones typically include carbon-carbon linkages and, in some embodiments, can also include one or more of amide, amine, ester, ether, ketone, peptide, or sulfide linkages, or combinations thereof. Examples of suitable polymer backbones include polyesters, polycarbonates, polyamides, polyethers (e.g., polyoxyethylene), polysulfones, polyurethanes, polyvinyl compounds (e.g., polystyrene, polyvinylchloride, poly(meth)acrylates, polyvinylpyrrolidone or polyacrylamides), polyimides or copolymers containing any combination of the representative monomer groups. Typical backbones are formed from the polymerization of monomers having ethylenically unsaturated (vinyl) bonds formed from the polymerization of, for example, acrylate monomers, such as methacrylate and ethacrylate monomers; acrylamide monomers, such as methacrylamide monomers; itaconate monomers; and styrene monomers.

Preferred polymer backbones provide the coating formed from the thermally-reactive polymer with one or more desired features, for example, lubricity and/or passivity against protein adsorption. In a preferred embodiment the polymeric backbone is formed by the polymerization of monomeric units of acrylamide and/or acrylamide derivatives, such as hydroxyethyl(meth)acrylate (HEMA). Acrylamide derivatives include, but are not limited to, monomers such as N,N-dimethylacrylamide, aminopropylmethacrylamide and dimethylaminopropylmethacrylamide. Other preferred polymer backbones are formed by the polymerization of monomeric units of vinylpyrrolidone and/or vinylpyrrolidone derivatives. The polymer backbone can be formed of similar polymerized monomeric units, for example, a homopolymeric backbone such as poly(aminopropylmethacryl-amide)) or more typically formed of different polymerized monomeric units (for example, a heteropolymeric backbone such as poly(acrylamide-co-N,N-dimethylamino-propylmethacryla-mide)).

Examples of other suitable polymeric backbones include, but are not limited to, poly(ethylene glycol) (PEG), poly(ethyloxazoline), poly(propylene oxide), poly(vinyl alcohol) (PVA), copolymers thereof, and the like.

Other useful polymer backbones include polyimine polymers, polylysine, polyomithine, polyethylenimine, polyamidoamine, polypropylenimine, and polyamine polymers or copolymers. Suitable polyamines are commercially available, for example, Lupasol™ PS (polyethylenimine; BASF, New Jersey).

In some cases it may be desirable to use naturally occurring polymers as the backbone for the thermally-reactive polymer. Suitable naturally-occurring polymeric backbones include polysaccharides, examples of which include, but are not limited to, hyaluronic acid (HA), starch, dextran, heparin, and chitosan; and proteins (and other polyamino acids), examples of which include, but are not limited to, gelatin, collagen, fibronectin, elastin, laminin, albumin, and active peptides of these proteins. In order to make thermally-reactive polymers having naturally occurring backbones, thermally-reactive groups can be coupled to pendent reactive groups on the naturally occurring polymeric backbone. For example, thermally-reactive groups can be coupled to collagen via reaction of amine containing lysine residues with halogenated peroxide-containing compounds as described herein.

In some aspects, a composition that includes the thermally-reactive polymer can also include another, different, thermally-reactive polymer. The other thermally-reactive polymer can include, for example, different thermally-reactive groups, a different polymeric backbone, or both different thermally-reactive groups and a different polymeric backbone. The other thermally-reactive polymer can be formed from any of the thermally-reactive groups and polymers described herein.

The polymeric backbone can include groups useful for coupling thermally-reactive groups and other groups that can provide additional functionality to the polymer. Suitable reactive groups include acid (or acyl) halide groups, alcohol groups, aldehyde groups, alkyl and aryl halide groups, amine groups, carboxyl groups, and the like. Particularly useful groups include amine groups such as primary, secondary, or tertiary amine groups. These pendent reactive groups can be used for the coupling chemical groups containing functional groups such as quaternary amine groups. In some embodiments these reactive groups can be used for coupling other functional groups such as sulfonate groups and lysine groups.

According to the invention, most or all of the linkages of polymeric backbone of the thermally-reactive polymer are thermally stable. Typically, the thermally-reactive polymer has a backbone that consists essentially of thermally-stable linkages. In alternate embodiments, the polymeric backbone can include one or more thermally-reactive linkages. For example, in some cases thermally-reactive groups can be pendent from either or both termini of the polymer.

In these embodiments the thermally-reactive polymer having thermally-reactive groups in its backbone can be heated to cause decomposition of the thermally-reactive polymer into smaller polymer fragments, the smaller polymer fragments having at least one terminus that is able to form a reactive group upon decomposition, which then can then cause the formation of a coated layer on the surface of a device. According to this embodiment, the backbone of the thermally-reactive polymer generally contains one or more thermally-reactive portions that are among the thermally-stable portions. The polymer fragments that are formed upon heating the thermally-reactive polymer are able to provide the surface with one or more desirable properties such as lubricity, passivity against protein absorption and/or bacterial adherence, and anti-microbial properties. It is preferred that the thermally-reactive polymer degrades into polymeric products having a Mw of about 1000 Da or greater.

In some embodiments, the thermally-reactive polymer of the current invention is generally of a size sufficient to provide a coated surface with intended properties, such as wettability, lubricity, passivity against protein adsorption, passivity against microbial adherence, anti-microbial properties, or any combination of any of these properties. Particularly useful polymer sizes are about 1000 Da or greater, for example, in the range of about 1000-1,000,000 Da. A more preferred size is about 5000 Da or greater.

The molecular weight of the thermally-reactive polymer refers to the molecular weight of the entire thermally-reactive polymer including the backbone, the thermally-reactive group, and any additional portion of the thermally-reactive polymer, unless otherwise noted herein.

The molecular weight of the polymer is more precisely defined as "weight average molecular weight" or $M_w$. $M_w$ is an absolute method of measuring molecular weight and is particularly useful for measuring the molecular weight of a polymer (preparation), such as preparations of thermally-reactive polymers. Polymer preparations typically include polymers that individually have minor variations in molecular weight. Polymers are molecules that have a relatively high molecular weight and such minor variations within the polymer preparation do not affect the overall properties of the polymer preparation (for example, the characteristics of an thermally-reactive polymer preparation). The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

In most embodiments, the thermally-reactive groups are pendent from the polymer backbone. "Pendent" generally refers to the attachment of one or more chemical groups, such as thermally-reactive groups, to the polymer backbone, but not necessarily within the polymer backbone. "Pendent" can be used to define the location of chemical group attachment on the polymer. For example, chemical groups can be pendent on the backbone anywhere along its length, or pendent at either terminus of the backbone, or both.

One or more thermally-reactive groups can be pendent along the polymer backbone at any position and can be spaced in a random or ordered manner. In addition, depending on the type of reactive groups on the polymer (or on monomers used for synthesis of the polymer), more than one thermally-reactive group can be pendent from a particular monomeric unit of the thermally-reactive polymer.

The invention also provides different approaches for the synthesis of the thermally-reactive polymer. One approach involves reacting a compound containing a thermally-reactive group, such as a peroxide-containing compound, with a polymer, thereby forming a polymer having a pendent thermally-reactive group. Another approach involves synthesizing a polymerizable monomer coupled to a thermally-reactive group and then polymerizing the monomer, typically with other monomers, using non-thermal polymerization techniques to form a polymer having pendent thermally-reactive groups.

In some cases the thermally-reactive group can be attached to a "preformed" polymer. The preformed polymer or copolymer can be obtained from a commercial source or be synthesized from the polymerization of a desired monomer or combination of different monomers. In one example of preparing the thermally-reactive polymer, the thermally-reactive groups are reacted with and attached, for example, by covalent bonding, to chemical groups pendent from the backbone of a polymer or copolymer. Such attachments of the thermally-reactive groups can be achieved by, for example, substitution or addition reactions.

In one embodiment, the thermally-reactive polymer is prepared by the nucleophilic coupling of a compound having a thermally-reactive group to a group pendent from the backbone of the polymer. For example, a halogenated compound containing a thermally-reactive group is reacted with a polymer having pendent amine groups. Next, an iodinated compound having a thermally-reactive peroxyester group is reacted with a polymer having a pendent amine group to provide a thermally-reactive polymer (referred to as "iodoamine coupling"). The invention demonstrates that this method of coupling can proceed to near completion and provide a thermally-reactive polymer with an amount of thermally-reactive groups that is sufficient to allow for the polymer to be coupled to the surface of a substrate after heating the polymer. It has been discovered that this method provides efficient coupling of the peroxyester moiety to the backbone of the polymer, particularly in comparison to other conventional coupling methods. Without being bound by theory, it is thought that the success of this synthetic scheme was a result of favorable steric features in the reactants.

The thermally-reactive polymer can be prepared using highly derivatizable preformed polymer as the polymer backbone. Preferred polymers contain a high number of reactive (derivatizable) groups, such as primary amine groups, relative to the molecular weight of the polymer. Suitable polymers and copolymers include amine-containing monomeric units such as acrylamide and vinylpyrrolidone derivatives.

In other cases polymerizable monomers having thermally-reactive groups are first synthesized and then the monomers are polymerized, thereby providing a polymer having thermally-reactive groups. Preferred monomers include thermally-reactive peroxide-containing groups. In some embodiments, monomers having thermally-reactive groups can be copolymerized with different monomers to create thermally-reactive polymers having one or more desired properties. For example, thermally-reactive copolymers can be prepared having properties such as lubricity and passivity against protein adsorption.

In view of the inventive details and methods of synthesis described herein, or in combination with other methods of synthesis known in the art, thermally reactive polymers can be prepared having a desired molar percentage of monomers with thermally-reactive groups, and/or a desired molar percentage of co-monomers.

In another specific embodiment, the invention provides a thermally-reactive polymer having a) a backbone including thermally-stable linkages, b) a quaternary amine group, and c) a thermally-reactive group. In preferred embodiments, upon application of heat, the polymer decomposes into products comprising a polymer-coupled radical species and a second radical species. The quaternary amine group can also be pendent from the polymer backbone. Upon decomposition of the thermally-reactive group the quaternary amine group remains pendent from the polymer backbone, that is, the quaternary amine group is not separated from the polymer backbone when the polymer-coupled radical species and the second radical species are formed. Therefore, the resulting polymeric coatings on surfaces formed by using this thermally-reactive polymer present quaternary amine groups. Quaternary amine-containing thermally-reactive polymers are shown herein to be useful for various purposes, including impeding microbial adherence on a surface and providing anti-microbial properties.

Quaternary amine groups can be formed on the thermally-reactive polymer using any of a number of synthetic methods. In one method polymers having pendent tertiary amine groups, can be reacted with halogenated alkanes to quaternize the amine group via the Menshutkin reaction. In some synthetic schemes, quaternization can be performed at the same time that coupling of a thermally-reactive group is performed. Quaternary amines can also be formed by reacting a thermally-reactive group, for example a halogenated alkyl peroxide, with a tertiary amine, which can provide a quaternary amine group and a thermally-reactive group pendent from a single arm of the polymer backbone.

The quaternary amine-containing thermally-reactive polymer includes quaternary amine group an amount sufficient to provide an anti-microbial effect and/or impede the adherence of bacteria to a surface coated with the polymer. In some preferred embodiments the thermally-reactive polymer includes about 10 molar percent or more quaternary amine groups, and in more preferred embodiments an amount of quaternary amine groups in the range of about 50 molar percent to about 90 molar percent.

The thermally-reactive polymer can also have groups that provide the polymer with additional functionalities, for example, groups that improve the biocompatibility of the polymer. A sulfonate group is one example of a group that can improve polymer biocompatibility by mimicking the action of heparin, thereby providing anti-coagulant properties to the coated surface. Sulfonate can be incorporated into the polymer through use of, for example, sulfonate-functionalized acrylamide. Another useful group is lysine, which can serve as a receptor for particular proteins such as tissue plasminogen activator (TPA) and plasminogen. Lysine can be incorporated into the polymer through use of, for example, lysine-functionalized malemide. Other types of useful functional groups can be attached to the thermally-reactive polymer. Attachment of the functional group can occur before or after immobilization of the thermally-reactive polymer on a surface. Attachment of the functional group may be through any reactive group as taught in the art, e.g., amine, N-hydroxy succinimide (NOS), or aldehyde.

While the thermally-reactive polymer includes a pendent thermally-reactive group, other reactive groups are optional. While in some embodiments the thermally-reactive polymer can include functional or reactive groups other than the thermally-reactive group, in other embodiments particular types of groups are not included in the polymer. In one embodiment, the thermally-reactive polymer does not include an ethylenically unsaturated group. In another embodiment, the thermally-reactive polymer does not include a polymerizable group. These are groups that are capable of undergoing a free radical polymerization reaction in response to a polymerization initiator and are not activated to a free radical form by thermal energy used to activate the thermally-reactive groups as described herein.

The thermally-reactive groups are useful for coupling a thermally-reactive polymer to the surface of a substrate. Methods for coating substrates with thermally-reactive polymers and the substrates coated with the thermally-reactive polymers are also provided within the scope of the invention and are described herein.

In another aspect, the invention provides methods for coating a surface of a substrate with the thermally-reactive polymer. The method includes the steps of a) providing a polymer that includes i) a backbone having thermally-stable linkages and ii) a thermally-reactive group; b) contacting the thermally-reactive polymer to the surface; and c) heating the polymer, wherein the polymer decomposes into products comprising a polymer-coupled radical species and a second radical species and the polymer-coupled radical species becomes associated with the surface of the article. In some embodiments the polymer-coupled radical species covalently bonds to the surface, and in other embodiments the polymer-coupled radical species covalently bonds to a target moiety to form a coated layer.

Optionally, steps in this coating method can be repeated, or additional steps can be added, to provide a desired coating to a surface. The thermally-reactive polymers and substrates described herein can be used in this method.

Typically, the thermally-reactive polymer is provided to the surface in an appropriate solvent or dispersant. The liquid solvent can be aqueous or organic. In some embodiments it is preferred to utilize an organic solvent. The thermally-reactive polymer is dissolved at a concentration sufficient to provide a coating of polymeric material to the surface. In one embodiment the thermally-reactive polymer is provided at a concentration of about 0.5 mg/ml or greater. In a specific embodiment the thermally-reactive polymer is provided at a concentration in the range of about 0.5 to about 10 mg/ml, and in a more specific embodiment in the range of about 0.5 to about 2.0 mg/ml.

In one embodiment, the method of coating a surface includes contacting the surface with the polymer, which is generally dissolved in a solvent, and then drying the solvent, which contains the polymer, on the surface. The process of drying generally refers to the removal of solvent from the solvent/polymeric composition to a desired moisture level. The thermally-reactive polymer can dry on the surface with or without activation of the thermally-reactive groups. The step of drying can include drying by heat or drying in a vacuum. In some methods utilizing heat drying, the drying temperature can be performed at or above the temperature that activates the thermally-reactive groups. Therefore, in these methods drying and covalently bonding can occur simultaneously.

In other embodiments the step of contacting the polymer to the surface and the step of heating the polymer is performed while the polymer is dissolved in a liquid phase, and a step of drying is not performed.

Prior to heating, it is desirable to keep the thermally-reactive polymer at a temperature where minimal decomposition of the thermally-reactive group occurs. Preferably, for example, the thermally-reactive polymer is stored at temperatures of 4° C. or less, and deposited on the article at temperatures of 25° C. or lower in a suitable solvent such as, for example, an aqueous solvent.

The thermally-reactive polymer can be provided to the entire surface of the substrate, or only a portion of the substrate, such as a portion of the surface that is intended to display properties consistent with the polymer-coating. Heating can be performed to covalently bond the polymer to a desired portion(s) of the surface.

In order to associate the thermally-reactive polymer with the surface, the thermally-reactive polymer is heated to a temperature that causes decomposition of the thermally-reactive groups and causes the formation of a polymer-coupled reactive species, for example, a polymer-coupled radical species. The polymer can be heated for a period of time that is sufficient to provide a desired polymeric coating to the surface. In some cases the thermally-reactive polymer is heated for shorter periods of time, for example, about one hour, or for longer periods of time, for example, greater than eight hours. It is understood that if the thermally-reactive polymer is heated for longer periods of time the heating may be performed at a lower temperature than situations wherein the thermally-reactive polymer is heated for shorter periods of time. The amount of time during which heat is applied can affect such features as the amount of polymer that is associated with the substrate surface, or the thickness of the coated layer.

In some embodiments, the step of heating is performed at a temperature of about 80° C. or higher, about 60° C. or higher, or about 40° C. or higher. In other, more particular embodiments wherein the thermally-reactive polymer provides a stable polymer-coupled radical species, heating can be performed at lower temperatures of about room temperature (about 25° C. or higher). For example, some thermally-reactive polymers having a thermally-reactive group that includes a peroxyester group and optionally a group that provides a stable polymer-coupled radical, for example a benzyl or diphenylacetyl radical, can have a decomposition temperature in the range of about 40° C. to 80° C. Reactivity of the thermally-reactive polymer can also be calculated by determining the rate of appearance of radical species caused by the decomposition of the thermally-reactive polymer. For example, the thermally reactive half-life of the polymer is determined by calculating the molar amount of thermally-reactive species on the thermally-reactive polymer and calculating the amount of a radical species produced after application of heat. Detection of the radical species can be determined, for example, by nuclear magnetic resonance or by a radical recombination assay using, for example, the compound DPPH (2,2-diphenyl-1-picrylhydrazyl radical). In one embodiment a polymer having a thermally-reactive peroxide-containing group has a half life of about 8.5 hours, or less, at 80° C.

Heat can be applied to the thermally-reactive polymer using any suitable source or method. The thermally-reactive polymer can be heated either directly, for example by direct radiation, or indirectly, through transfer of heat from one medium to another, such as in a water bath. Heating sources that provide infrared or microwave radiation, for example, can be used to activate the thermally-reactive groups on the polymer. Alternatively, devices that provide heat by increasing vibrational energy, such as sonicators, can also be used. Dry ovens, steam baths, water baths, heat lamps, sonicators, and pressure chambers can be used to provide heat to the thermally-reactive polymer.

The invention provides methods for forming a coating that can include one or more coated layers. In some embodiments, an article having more than one coated layer is provided, and can be formed using the methods described herein with or without other coating methods known in the art. If an article having multiple coated layers is formed, the individual coated layers can include similar or different types of polymeric materials. Coatings can include base coats and top coats, which typically having certain physical and functional properties, such as thickness, permeability, strength, and protectivity. Coatings may include bioactive agents (such as pharmaceuticals) that can be eluted or that are immobilized in the coating to provide some beneficial effect, e.g. hemocompatibility.

The thermally-reactive polymers of the invention are useful, for example, for coating substrates having complex geometries, such as surfaces of medical devices. The methods provided herein generally include use of heat to activate and covalently bond the thermally-reactive polymers to the surface. These methods can provide covalently bound polymer coatings to inner surfaces of small devices, wherein the inner surface may not be accessible to other forms of energy, such as light, which alternatively may be used to activate and bind coating reagents to surfaces. Coatings formed by physical adsorption methods may be less durable or have other undesirable characteristics, for example, flaking, that may be exhibited over time. Therefore, use of thermally-reactive polymers is advantageous as it can provide a uniform polymer coating to many substrates as well as substrates having complex geometries and inner surfaces.

"Surface" is used in its broadest sense and refers to any sort of surface of a substrate on which the thermally-reactive polymer can be provided to form a coated layer. According to the invention, the thermally-reactive polymer is heated, causing the thermally-reactive groups to covalently bond with a target moiety thereby forming a coated layer on the surface. In some embodiments, the thermally-reactive polymer is covalently bonded to the surface. The surface provides a source of abstractable hydrogen atoms allowing for this mechanism to take place. The abstractable hydrogen atoms can be provided by the material of the surface itself or by a base coat material that is deposited between the surface and the thermally-reactive polymer. The surface can be made of any suitable synthetic or natural materials or combinations thereof.

Synthetic surfaces include any useful man-made materials, such as functionalized and non-functionalized materials made of plastics, ceramic, resins, polysaccharides, silicon, or silica-based materials, glass, metals, films, gels, membranes, nylon, natural fibers such as silk, wool and cotton.

The thermally-reactive polymer of the invention can be utilized in connection with medical devices constructed from a variety of biomaterials. The thermally-reactive polymer can be disposed on devices constructed from one or more of these biomaterials to form a coated layer. Preferred biomaterials include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, and vinylidene difluoride. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketone.

Certain natural materials are also suitable biomaterials, including human tissue such as bone, cartilage, skin and teeth; and other organic materials such as wood, cellulose, compressed carbon, and rubber. Other suitable biomaterials include metals and ceramics. The metals include, but are not limited to titanium and tantalum, and noble metals such as gold, silver, copper, and platinum uridium. Alloys of metals, such as nitinol, stainless steel, and cobalt/chromium are suitable for biomaterials as well. The ceramics include, but are not limited to, silicon nitride, silicon carbide, zirconia, and alumina, as well as glass, silica, and sapphire.

Combinations of ceramics and metals are another class of biomaterials. Another class of biomaterials is fibrous or porous in nature.

The surface of biomaterials can also be pretreated in order to alter the surface properties of the biomaterial, when desired. Examples of suitable compounds that can be used to pretreat a surface include Parylene and organosilane compounds.

Biomaterials can be used to fabricate a variety of implantable devices. The medical device can be any device that is introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles, or atria of the heart.

Compositions of this invention can be used to coat the surface of a variety of implantable devices, for example: drug-delivering vascular stents; other vascular devices (e.g., grafts, catheters, valves, artificial hearts, heart assist devices, ventricular assist devices); implantable defibrillators; blood oxygenator devices and circuits; surgical devices; tissue-related materials; membranes; cell culture devices; chromatographic support materials; biosensors; shunts for hydrocephalus; wound management devices; endoscopic devices; infection control devices; orthopedic devices; dental devices, urological devices; colostomy bag attachment devices; ophthalmic devices; glaucoma drain shunts; synthetic prostheses; intraocular lenses; respiratory, peripheral cardiovascular, spinal, neurological, dental, ear/nose/throat devices (e.g., ear drainage tubes); renal devices; and dialysis devices (e.g., tubing, membranes, grafts).

Examples of useful devices include self-expanding stents (e.g., made from nitinol), balloon-expanded stents (e.g., prepared from stainless steel), degradable coronary stents, non-degradable coronary stents, peripheral coronary stents, endovascular stents, intraaortic balloons, urinary catheters (e.g., surface-coated with antimicrobial agents), penile implants, sphincter devices, urethral devices, bladder devices, renal devices, vascular implants and grafts, intravenous catheters (e.g., treated with antithrombotic agents), small diameter grafts, artificial lung catheters, electrophysiology catheters, pacemaker leads, anastomosis devices, vertebral disks, bone pins, suture anchors, hemostatic barriers, clamps, surgical staples/sutures/screws/plates/clips, atrial septal defect closures, electro-stimulation leads for cardiac rhythm management (e.g., pacer leads), glucose sensors (long-term and short-term), blood pressure and stent graft catheters, blood oxygenator tubing, blood oxygenator membranes, blood bags, birth control devices, breast implants, benign prostatic hyperplasia and prostate cancer implants, bone repair/augmentation devices, breast implants, cartilage repair devices, orthopedic joint implants, orthopedic fracture repairs, tissue adhesives, tissue sealants, tissue scaffolds, dental implants, dental fracture repair devices, implanted drug infusion tubes, intravitreal drug delivery devices, nerve regeneration conduits, oncological implants, electrostimulation leads, pain management implants, spinal/orthopedic repair devices, surgical blood salvage disposal sets, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricular assist devices, neuro aneurysm treatment coils, neurological catheters, left atrial appendage filters, central venous access catheters, hemodialysis devices, hemodialysis catheters, catheter cuff, anastomotic closures, vascular access catheters, cardiac sensors, intravascular sensors, uterine bleeding patches, urological catheters/stents/implants, in vitro diagnostics, aneurysm exclusion devices, neuropatches, Vena cava filters, urinary dialators, endoscopic surgical tissue extractors, atherectomy catheters, clot extraction catheters, PTA catheters, PTCA catheters, stylets (vascular and non-vascular), coronary guidewires, drug infusion catheters, esophageal stents, circulatory support systems, angiographic catheters, transition sheaths and dialators, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

It is understood that although the thermally-reactive polymers of the invention are particularly useful for forming a coated layer on the surface of medical devices, these polymers can also be used in combination with other articles, for example, any article suitable as a substrate for forming a coated layer that includes the thermally-reactive polymer.

The thermally-reactive polymers are particularly suitable for coating substrates that have "inner surfaces", which refers to surfaces wherein only a limited amount or no light can access as compared to an outer surface. Particular examples of substrates that have inner surfaces may include, for example, stents, catheters such as PTCA catheters and hemodialysis catheters, hemodialysis membranes, and other devices having inner surfaces. These substrates can be formed, for example, from a complex architecture of materials, or contain many pores.

In another aspect, the invention provides a composition that includes a thermally-reactive polymer, as described herein, and another component which can be useful for forming a polymeric layer on a surface. Compounds useful for forming a polymeric layer include, for example, polymerization accelerators, catalysts, crosslinking compounds, and secondary polymers. The composition with the thermally-reactive polymer can include one or more of these components, in an amount or amounts that provide the polymeric coating with desired properties.

The term "secondary polymer" refers to polymers that can be included in a coating along with the thermally-reactive polymer but that are different than the thermally-reactive polymer. Secondary polymers can include, for example, modified or unmodified polymers and can provide the coating that is formed using the thermally-reactive polymer with one or more additional properties. For example, a composition with the thermally-reactive polymer can include one or more secondary polymers, in an amount or amounts that provide the coating with desired properties. The backbone of the secondary polymer can be the same or different than that of the thermally-reactive polymer. For example, the secondary polymer can have a polymer backbone that is formed by polymerization of acrylamide and/or acrylamide derviatives. Another example of a useful secondary polymer is a polymer that includes vinylpyrrolidone and/or similar compounds. In the process of forming a coating, in some embodiments the thermally-reactive polymer can become covalently bonded to the secondary polymer via the thermally-reactive groups.

In other embodiments a crosslinking compound can be included in the coating along with the thermally-reactive polymer. Preferred compositions include a thermally-reactive crosslinking compound having a peroxide-containing thermally-reactive group. Examples of crosslinking compounds containing peroxide groups include dialkyl peroxides and peroxyketals, which are commercially available. One suitable thermally-reactive crosslinking molecule is 2,4-pentanedione peroxide (Luperox 224; Atofina Chemicals, Philadelphia, Pa.). One particularly useful coating composition includes a thermally-reactive polymer, a secondary polymer, and a thermally-reactive crosslinking compound.

Upon heating the composition, the secondary polymer can become crosslinked to the thermally-reactive polymer via the thermally-reactive crosslinking molecule, and the crosslinked polymers can then in turn be immobilized on the surface of the substrate through the thermally-reactive groups. Use of this type of composition can be particularly advantageous as it can provide a cost-effective way to provide a surface coating since many non-derivitized polymers are inexpensive and commercially available. The secondary polymer can provide the bulk of any desirable physical properties, such as lubricity and passivity against protein adsorption.

Compositions that include the thermally-reactive polymer and the secondary polymer at various ratios can be prepared and used to coat a surface. Useful ranges of thermally-reactive to secondary polymer include, for example, from about a 1:5 to about a 5:1 ratio. The thermally-reactive crosslinking molecule in an amount from about 0.5 to about 5 wt. % of the overall polymer composition can also be used.

In some embodiments a bioactive agent can be included in the coating on the surface of the article. These agents can be present in the same coated layer as the thermally-reactive polymer, or, in the case that the coated article has more than one coated layer, can be present in another coated layer.

The bioactive agent may be released from the coating by particle dissolution or diffusion if the coating includes biologically-stable materials, for example, a biologically stable thermally-reactive polymer. Alternatively, one or more bioactive agents can be presented to the physiological environment without being released from the coated surface. For example, the bioactive agent(s) can be covalently coupled to the thermally-reactive polymer so that the bioactive agent(s) are not released from the polymeric material into the physiological environment.

The term "bioactive agent" refers to a peptide, protein, carbohydrate, nucleic acid, lipid, polysaccharide or combinations thereof, or synthetic inorganic or organic molecule, that causes a biological effect when administered in vivo to an animal, including but not limited to birds and mammals, including humans. Nonlimiting examples are antigens, enzymes, hormones, receptors, peptides, and gene therapy agents. Examples of suitable gene therapy agents include (a) therapeutic nucleic acids, including antisense DNA and antisense RNA, and (b) nucleic acids encoding therapeutic gene products, including plasmid DNA and viral fragments, along with associated promoters and excipients. Examples of other molecules that can be incorporated include nucleosides, nucleotides, vitamins, minerals, and steroids.

Classes of bioactive agents which can be incorporated into coatings of this invention include, but are not limited to: ACE inhibitors, actin inhibitors, analgesics, anesthetics, anti-hypertensives, anti-polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidants, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, opioids, photodynamic therapy agents, prostaglandins, remodeling inhibitors, statins, steroids, thrombolytic agents, tranquilizers, vasodilators, and vasospasm inhibitors. A more complete listing of classes of medicaments may be found in the Pharmazeutische Wirkstoffe, ed. A. Von Kleemann and J. Engel, Georg Thieme Verlag, Stuttgart/New York, 1987, incorporated herein by reference.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforamide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Anti-viral agents are substances capable of destroying or suppressing the replication of viruses. Examples of anti-viral agents include α-methyl-P-adamantane methylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostiginine sulfate, tacrine HCl, tacrine, 1-hydroxymaleate, iodotubercidin, p-bromotetramisole, 10-(a-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl, L(−), deprenyl.HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−), alpha-methyltyrosine, D L(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances which have an anesthetic effect in a localized region. Examples of such anesthetics include procaine, lidocaine, tetracaine and dibucaine.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Examples of statins include lovastatin, pravastatin, simvastatin, fluvastatin, atorvastatin, cerivastatin, rousvastatin, and superstatin.

Imaging agents are agents capable of imaging a desired site, e.g., tumor, in vivo, can also be included in the coating composition. Examples of imaging agents include substances having a label which is detectable in vivo, e.g., antibodies attached to fluorescent labels. The term antibody includes whole antibodies or fragments thereof.

In some aspects the bioactive agent can be selected to improve the compatibility (for example, with blood and/or surrounding tissues) of medical device surfaces. These agents, referred to herein as "biocompatible agents," when associated with the medical device surface, can serve to shield the blood from the underlying medical device material. Suitable biocompatible agents preferably reduce the likelihood for blood components to adhere to the medical device, thus reducing the formation of thrombus or emboli (blood clots that release and travel downstream).

The biocompatible agent can improve the biocompatibility of the medical article having a coating that includes the thermally-reactive polymer (although a coating having the thermally-reactive polymer may improve the biocompatible or hemocompatible properties of the device itself, without addition of a biocompatible agent). The biocompatible agent can provide antirestenotic effects, such as antiproliferative, antiplatelet, and/or antithrombotic effects. In some embodiments, the biocompatible agent can include anti-inflammatory agents, immunosuppressive agents, cell attachment factors, receptors, ligands, growth factors, antibiotics, enzymes, nucleic acids, and the like. Compounds having antiproliferative effects include, for example, actinomycin D, angiopeptin, c-myc antisense, paclitaxel, taxane, and the like.

Representative examples of biocompatible agents having antithrombotic effects (thrombin inhibitors) include heparin, heparin derivatives, sodium heparin, low molecular weight heparin, hirudin, lysine, prostaglandins, argatroban, forskolin, vapiprost, prostacyclin and prostacyclin analogs, D-phpr-arg-chloromethylketone (synthetic antithrombin), dipyridamole, glycoprotein IIb/IIIa platelet membrane receptor antibody, coprotein Ib/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like.

The biocompatible agent can also be an inhibitor of the GPIIb-IIIa platelet receptor complex, which mediates platelet aggregation. GPIIb/IIIa inhibitors can include monoclonal antibody Fab fragment c7E3, also know as abciximab (ReoPro™), and synthetic peptides or peptidomimetics such as eptifibatide (Integrilin™) or tirofiban (Agrastat™).

The biocompatible agent can be an immunosuppressive agent, for example, cyclosporine, CD-34 antibody, everolimus, mycophenolic acid, sirolimus, tacrolimus, and the like.

Additionally, the biocompatible agent can be a surface adhesion molecule or cell-cell adhesion molecule. Exemplary cell adhesion molecules or attachment proteins (such as extracellular matrix proteins including fibronectin, laminin, collagen, elastin, vitronectin, tenascin, fibrinogen, thrombospondin, osteopontin, von Willibrand Factor, bone sialoprotein (and active domains thereof), or a hydrophilic polymer such as hyaluronic acid, chitosan or methyl cellulose, and other proteins, carbohydrates, and fatty acids. Exemplary cell-cell adhesion molecules include N-cadherin and P-cadherin and active domains thereof.

Exemplary growth factors include fibroblastic growth factors, epidermal growth factor, platelet-derived growth factors, transforming growth factors, vascular endothelial growth factor, bone morphogenic proteins and other bone growth factors, and neural growth factors.

Exemplary ligands or receptors include antibodies, antigens, avidin, streptavidin, biotin, heparin, type IV collagen, protein A, and protein G.

Exemplary antibiotics include antibiotic peptides.

The biocompatible agent can be also be selected from mono-2-(carboxymethyl) hexadecanamidopoly (ethylene glycol)$_{200}$ mono-4-benzoylbenzyl ether, mono-3-carboxyheptadecanamidopoly (ethylene glycol)$_{200}$ mono-4-benzoylbenzyl ether, mono-2-(carboxymethyl) hexadecanamidotetra (ethylene glycol) mono-4-benzoylbenzyl ether, mono-3-carboxyhepta-decanam-idotetra (ethylene glycol) mono-4-benzoylbenzyl ether, N-[2-(4-benzoylbenzyloxy) ethyl]-2-(carboxymethyl) hexadecanamide, N-[2-(4-benzoylbenzyloxy) ethyl]-3-carboxyheptadecanamide, N-[12-(benzoylbenzyloxy) dodecyl]-2-(carboxymethyl) hexadecanamide, N-[12-(benzoylbenzyloxy) dodecyl]-3-carboxy-heptadecanamide, N-[3-(4-benzoylbenzamido) propyl]-2-(carboxymethyl) hexadecanamide, N-[3-(4-benzoylbenzamido) propyl]-3-carboxyheptadecanamide, N-(3-benzoylphenyl)-2-(carboxymethyl) hexadecanamide, N-(3-benzoylphenyl)-3-carboxyheptadecanamide, N-(4-benzoylphenyl)-2-(carb-oxymethyl) hexadecanamide, poly (ethylene glycol)$_{200}$ mono-15-carboxypentadecyl mono-4-benzoylbenzyl ether, and mono-15-carboxypentadecanamidopoly (ethylene glycol)$_{200}$ mono-4-benzoylbenzyl ether.

Additives such as inorganic salts, BSA (bovine serum albumin), and inert organic compounds can be used to alter the profile of bioactive agent release, as known to those skilled in the art.

Additional examples of contemplated bioactive agents and/or bioactive agent include sirolimus (rapamycin), analogues of rapamycin ("rapalogs"), tacrolimus (FK-506), ABT-578 from Abbott, dexamethasone, betamethasone, vinblastine, vincristine, vinorelbine, poside, teniposide, daunorubicin, doxorubicin, idarubicin, anthracyclines, mitoxantrone, bleomycins, plicamycin (mithramycin), mitomycin, mechlorethamine, cyclophosphamide and its analogs, melphalan, chlorambucil, ethylenimines and methylmelamines, alkyl sulfonates-busulfan, nitrosoureas, carmustine (BCNU) and analogs, streptozocin, trazenes-dacarbazinine, methotrexate, fluorouracil, floxuridine, cytarabine, mercaptopurine, thioguanine, pentostatin, 2-chlorodeoxyadenosine, cisplatin, carboplatin, procarbazine, hydroxyurea, mitotane, estrogen, ticlopidine, clopidogrel, abciximab, breveldin, cortisol, cortisone, fludrocortisone, prednisone, prednisolone, 6U-methylprednisolone, triamcinolone, acetaminophen, etodalac, tolmetin, ketorolac, ibuprofen and derivatives, mefenamic acid, meclofenarnic acid, piroxicam, tenoxicam, phenylbutazone, oxyphenthatrazone, nabumetone, auranofin, aurothioglucose, gold sodium thiomalate, azathioprine, mycophenolate mofetil; angiotensin receptor blockers; nitric oxide donors; and mTOR inhibitors.

A comprehensive listing of bioactive agents can be found in *The Merck Index*, Thirteenth Edition, Merck & Co. (2001). Bioactive agents are commercially available from Sigma Aldrich Fine Chemicals, Milwaukee, Wis.

The concentration of the bioactive agent or agents can be in the range of about 0.01 to about 90 percent, by weight, based on the weight of the final coated composition. The particular bioactive agent, or combination of bioactive agents, can be selected depending upon one or more of the following factors: the application of the medical device, the medical condition to be treated, the anticipated duration of treatment, characteristics of the implantation site, the number and type of bioactive agents to be utilized, and the like.

In another embodiment of the invention, one or more bioactive agents can be disposed on the surface of the device in association with the thermally-reactive polymer. A coating formed on the surface can include a thermally-reacted polymer and a bioactive agent. In the coating, the thermally reacted polymer and the bioactive agent can be present in the same and/or different coated layers.

In one particular embodiment, the coating includes a thermally-reactive polymer and a bioactive agent that is sensitive to light irradiation (a light-sensitive bioactive agent). For example, a bioactive agent that can become partially or fully inactivated by exposure to light irradiation can be present in a coating that includes the thermally-reactive polymer. In the process of forming the inventive coating, use of light wavelength that may result in the inactivation of the bioactive agent can be avoided. According to the invention, heat, or another form of energy that activates the thermally reactive group, is applied to form the coating, which does not result in a loss of a significant amount of activity from the bioactive agent.

In another embodiment, the invention provides a method for improving the lubricity of surface of a substrate. A substrate having a coating that provides improved lubricity will encounter less frictional resistance when moved within a portion of the body, as compared to an uncoated substrate. Lubricity can also be important for devices with inner moving parts in addition to devices that function along with another device, for example, a coronary catheter which guides the insertion of a PTCA catheter.

Improved lubricity can be shown by a reduction in the water contact angle on polymer-coated surfaces in comparison to uncoated surfaces. Reduction of water contact angle is indicative of increased wettability, which associates with an improvement in lubricity.

Therefore, a method for improving lubricity on surfaces includes the steps of a) providing a polymer that includes i) a backbone having thermally-stable linkages and ii) a thermally-reactive group; b) contacting the polymer to the surface; and c) heating the polymer to form a polymer coated surface. In some embodiments the polymer decomposes into products comprising a polymer-coupled radical species and a second radical species and the polymer-coupled radical species covalently binds to the surface forming a polymer-coated surface. The water contact angle is reduced in the range of about 25° to about 60° on a polymer-coated surface compared to an uncoated surface. The method is particularly useful for improving the lubricity of substrates such as medical devices that can be introduced into the body and that are subject to some sort of movement in the body.

In other more specific embodiments, a polymer-coated surface having increased lubricity, formed according to the methods of the invention, can additionally have the property of maintaining an improvement in lubricity following physical challenge. For example, the coated surface can be physically challenged by rubbing the surface, wherein, after rubbing, the coated surface exhibits a reduced water contact angle (for example, reduced by 28% or greater) as compared to an uncoated surface.

In another embodiment, the method for improving the lubricity is performed by providing a thermally-reactive polymer that includes 5 molar percent or more thermally-reactive groups. More specifically, the method is performed by providing a thermally-reactive polymer that includes in the range of 5 molar percent to 40 molar percent thermally-reactive groups.

In other embodiments, the invention also provides thermally-reactive polymers that can be used to improve the lubricity of coated surfaces as well as the resulting polymer-coated surfaces that have improved lubricity.

In another embodiment, the invention provides a method for passivating against protein adsorption on a surface. Reduction of protein adsorption on a surface is desirable, for example, in order to prevent clogging or fouling of a substrate. For example, in some cases, surfaces having improved passivity against protein adsorption can lessen the need for a patient having the coated device to receive anticoagulant drugs.

The method includes the steps of a) providing a polymer that includes i) a backbone having thermally-stable linkages and ii) a thermally-reactive group; b) contacting the polymer to the surface; and c) heating the polymer to form a polymer-coated surface. In some embodiments the polymer decomposes into products comprising a polymer-coupled radical species and a second radical species and the polymer-coupled radical species covalently binds to the surface. Protein adsorption is reduced by about 35% or greater on the polymer coated surface as compared to an uncoated surface. The method is particularly useful for passivating against protein adsorption on substrates such as medical devices to prevent clogging and fouling of the devices in the body.

In more specific embodiments the method for passivating against protein adsorption provides a polymer-coated surface wherein protein adsorption is reduced in the range of about 35% to about 76% as compared to an uncoated surface.

In one embodiment, a surface having passivity against protein adsorption prepared providing a coating composition including a thermally-reactive polymer, wherein the thermally-reactive polymer is present at a concentration of 0.5 mg/ml or greater in the coating composition. In a specific embodiment the thermally-reactive polymer is provided at a concentration in the range of about 0.5 to about 5 mg/ml, and in a more specific embodiment in the range of about 0.5 to about 2 mg/ml.

In another embodiment the invention provides methods for passivating against protein adsorption on a substrate wherein the substrate includes a plastic, and in a more specific embodiment the plastic is selected from the group consisting of polyvinylchloride (PVC), polyurethane (PU), polyethylene (PE), polypropylene (PP), low density polyethylene (LdPE), and combinations thereof.

In other embodiments, the invention also provides thermally-reactive polymers that provide passivity against protein adsorption on a surface and polymer-coated surfaces that have improved passivity against protein adsorption.

In another embodiment, the invention provides a method for impeding microbial adherence on a surface. This method can prevent clogging or fouling of substrates, such as medical devices, due to bacterial adherence and any sort of immune system-produced substance that may be deposited on the substrate. The method includes the steps of a) providing a polymer that includes i) a backbone having thermally-stable linkages and ii) a thermally-reactive group; b) contacting the polymer to the surface; and c) heating the polymer to form a polymer-coated surface. In some embodiments the polymer decomposes into products comprising a polymer-coupled radical species and a second radical species and the polymer-coupled radical species covalently binds to the surface forming a coated layer. The polymer-coated surface exhibits reduced bacterial adherence relative to an uncoated control.

In some specific embodiments for impeding microbial adherence on a surface the thermally-reactive polymer includes a peroxide group. In a more specific embodiment the thermally-reactive group is a peroxyester group and the polymer has at least 10% molar peroxyester content.

In some specific embodiments the polymer includes a quaternary amine group and in more specific embodiments the polymer includes at least 10% molar quaternary amine content.

The invention will now be demonstrated referring to the following non-limiting examples.

EXAMPLE 1

Synthesis of Halogenated Perester Compounds

This example describes the synthesis of halogenated peroxyester compounds, which where then utilized for the synthesis of polymer having thermally activatable peroxyester groups.

I. Synthesis of 6-bromohexanoyl t-butyl Peroxyester

All reagents were purchased from Aldrich Chemical, St. Louis, Mo. unless otherwise indicated. Two batches of 6-bromohexanoyl t-butyl peroxyester were prepared, generally according to the same method with the synthesis taking place at room temperature (approximately 25-27° C.), and with some variation in the reaction conditions and concentrations of reagents. NMR analysis showed that the 6-bromohexanoyl t-butyl peroxyester products of batch A and B were indistinguishable.

A. Batch A: 6-bromohexanoyl chloride (3.339 g; 15.6 mmole) was dissolved in 100 ml of anhydrous THF under a nitrogen atmosphere. 5 ml of 5.0M t-butylhydroperoxide in decane (25 mmole) was added via syringe, followed by the dropwise addition of 2.4 ml of 1,8-diazabicyclo[5.4.0]undec-7-ene (DBU) (15.6 mmole), which resulted in the formation of a white precipitate (protonated DBU salt) which was filtered off and discarded. The reaction was stirred at room temperature, under a nitrogen atmosphere for three hours, after which it was filtered and concentrated to remove the solvent and excess t-butylhydroperoxide.

$^1$H NMR was performed using a Bruker 400 MHz NMR to confirm formation of 6-bromohexanoyl t-butyl peroxyester product which showed the following shifts relative to TMS, in $CDCl_3$: 3.42 ppm (multiplet, 2H), 2.35 ppm (multiplet, 2H), 1.87 ppm (multiplet, 2H), 1.73 ppm (multiplet, 2H), 1.50 ppm (multiplet, 2H), 1.34 ppm (singlet, 9H). The 6-bromohexanoyl t-butyl peroxyester was used in the subsequent step without further purification.

B. Batch B: A second batch of 6-bromohexanoyl t-butyl peroxyester was prepared using the same procedure as detailed in I.A., with the following exceptions: 50 ml of 6-bromohexanoyl chloride (13.1 mmole) in THF was combined with 5 ml of 5.0M t-butylhydroperoxide followed by the dropwise addition of 2 ml DBU (13.4 mM). The mixture was stirred under nitrogen for two hours.

NMR data showed the following shifts: 3.42 ppm (multiplet, 2H), 2.35 ppm (multiplet, 2H), 1.87 ppm (multiplet, 2H), 1.73 ppm (multiplet, 2H), 1.50 ppm (multiplet, 2H), 1.34 ppm (singlet, 9H); which is identical to the NMR data of the 6-bromohexanoyl t-butyl peroxyester product of I.A.

II. Finkelstein Conversion to 6-iodohexanoyl t-butyl Peroxyester

A. The following steps were performed at room temperature. Approximately 4 grams of the 6-bromohexanoyl t-butyl peroxyester preparation from I.A. was dissolved in 20 ml of acetone. A solution of 4.69 g sodium iodide (31.3 mmole) in 20 ml of acetone was added to the peroxyester solution. Immediate precipitation of sodium bromide occurred as well as formation of a dark red color. The reaction was stirred overnight (subsequent reactions revealed that 30 minutes was sufficient for the reaction to go to completion). The reaction mixture was chilled, then filtered by gravity and the volume was reduced by evaporating off acetone. The mixture containing the reaction product was then re-dissolved in 50 ml of chloroform and washed four times with 50 ml of 1% w/v sodium thiosulfate aqueous solution, then twice with 50 ml of deionized water. The organic layer was dried over sodium sulfate and the solvent was removed by rotary evaporation. The yield of the 6-iodohexanoyl t-butyl peroxyester product was 4.0 g (82% total). $^1$H NMR shifts relative to TMS, in $CDCl_3$ were: 3.20 ppm (multiplet, 2H), 2.35 ppm (multiplet, 2H), 1.87 ppm (multiplet, 2H), 1.73 ppm (multiplet, 2H), 1.50 ppm (multiplet, 2H), 1.34 ppm (singlet, 9H). The 6-bromohexanoyl t-butyl peroxyester (Compound 1) is shown below:

(Compound 1)

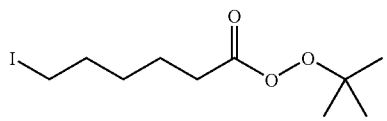

B. A second batch of 6-iodohexanoyl t-butyl peroxyester was prepared using the same procedure as detailed in II.A., with the following exceptions. A solution of sodium iodide (20.2 mmole), dissolved in 15 ml of acetone, was added to approximately 3 grams of 6-bromohexanoyl t-butyl peroxyester preparation from I.B. dissolved in 20 ml of acetone. During purification of the product, the organic layer was dried over magnesium sulfate.

$^1$H NMR shifts relative to TMS, in $CDCl_3$ were: 3.20 ppm (multiplet, 2H), 2.35 ppm (multiplet, 2H), 1.87 ppm (multiplet, 2H), 1.73 ppm (multiplet, 2H), 1.50 ppm (multiplet, 2H), 1.34 ppm (singlet, 9H); which was identical to the NMR data of the 6-bromohexanoyl t-butyl peroxyester product of I.A.

EXAMPLE 2

Synthesis of an Acrylamide-Based Polymers

Acrylamide-based copolymers were prepared as a reagent used for the synthesis of peroxyester polymers, as described herein.

I. Synthesis of DMA:APMA Copolymer

Poly (N,N-dimethylacrylamide-co-aminopropylmethacrylamide) (DMA:APMA) was synthesized by radical polymerization with the chain transfer reagent mercaptoethanol. A solution of 4.25 ml N,N-dimethylacrylamide (DMA), 70 µl of mercaptoethanol, 0.8384 g aminopropyl methacrylamide (APMA), 0.3288 g 2,2'-azo-bis-isobutyrylnitrile (AIBN), and 47 µl N,N,N',N'-tetramethyl-ethylenediamine (TEMED) in 41.6 ml of dimethyl sulfoxide (DMSO) was sparged with helium for five minutes to remove oxygen and heated to 60° C. for 15 hours. After heating, the polymer was transferred to 1000 MW dialysis tubing (Spectrum Laboratories, Rancho Dominguez, Calif.) and continuous flow dialysis was performed. The resulting polymers had either a 90:10 or 84:16 mole ratio of DMA to APMA, with a molecular weight (Mw) of approximately 5000. The product was lyophilized after three days to give a white powder and gave a yield of 2.28 g. $^1$H NMR shifts relative to TMS, in DMSO-$d_6$ were 7.61 ppm, 300 ppm, 2.79 ppm, 1.50 ppm, 1.12 ppm, 0.82 ppm, 0.72 ppm. All NMR peaks were very broad due to polymerization. No multiplicity assignment or integrations were possible due to overlap.

II. Synthesis of AA:DMAPMA Copolymer

Poly (acrylamide-co-N,N-dimethylaminopropylmethacrylamide) (AA: DMAPMA) was synthesized by radical polymerization with the chain transfer reagent mercaptoethanol. A solution of 2.81 g acrylamide, 140 µl of mercaptoethanol, 7.04 g N,N-dimethylaminopropyl methacrylamide, 0.0992 g AIBN, and 0.0831 g TEMED in 73 ml of DMSO was sparged with argon for four minutes to remove oxygen and heated to 58° C. for 15 hours. After heating the polymer was transferred to continuous flow dialysis with 1000 MW dialysis tubing. The resulting polymer was approximately 50:50 mole ratio of acrylamide to DMAPMA, with a molecular weight of approximately 5000. The product was lyophilized after three days to give a white powder, yield: 7.65 g. $^1$H NMR shifts relative to TMS, in DMSO-$d_6$: 7.54 ppm (1H), 7.0 ppm (1H), 6.71 ppm (1H), 3.01 ppm (2H), 2.12 ppm (8H), 1.52 ppm (5H), 0.84 ppm (4H). All NMR peaks were very broad due to polymerization. No multiplicity assignments were made. All integrations were approximate.

III. Synthesis of PVP:DMAPMA Copolymer

Poly (polyvinylpyrrolidone-co-N,N-dimethylaminopropylmethacrylamide) (PVP: DMAPMA) was synthesized by radical polymerization. A mixture of 3.75 ml N-vinyl pyrrolidone, 2.75 ml N,N-dimethylaminopropyl methacrylamide, and 0.122 g Vazo 67 (initiator) in 36 ml of DMSO was sparged with nitrogen for 10 minutes to remove oxygen and heated to 55° C. for 13 hours. After heating the polymer was diluted with deionized water and transferred to continuous flow dialysis using 3500 MW dialysis tubing. The polymer was dialyzed for three days, then lyophilized to give a white powder, the yield being 4.70 g. $^1$H NMR shifts relative to TMS, in DMSO-$d_6$ were: 7.3 ppm (2H), 3.0 ppm (9H), 2.2 ppm (20H), 1.8 ppm (6H), 1.6 ppm (3H), 1.5 ppm (9H), 0.8 ppm (8H). All NMR peaks were very broad due to polymerization. No multiplicity assignments were made and all integrations were approximate. Based on the NMR the ratio of PVP:DMAPMA was determined to be approximately to 40:60.

EXAMPLE 3

Synthesis of an Acrylamide-Based Polymers Having Pendent Thermally-Reactive Peroxyester Groups The halogenated peroxyester compounds, as described in Example 1, were attached to amine groups on acrylamide-based copolymers, as described in Example 2, through a nucleophilic reaction.

I. Synthesis of a DMA:APMA-Peroxyester Polymer

The following procedure was carried out to provide DMA:APMA polymers having pendent peroxyester groups.

DMA:APMA (0.5031 g; MW ~5000; 10 mole % APMA; 0.49 mmole of APMA) as described in Example 2, II., was dissolved in 5 ml DMSO. For a target 10 mole % peroxyester derivatization, a solution of 0.1614 g 6-iodohexanoyl t-butyl peroxyester (0.51 mmole) in 1 ml of DMSO was added to the polymer solution. For a target 20 mole % and 30 mole % peroxyester derivatization the amount of 6-iodohexanoyl t-butyl peroxyester molarity in solution was increased to 1.02 mmole and 1.53 mmole.

The reaction mixture was heated overnight at 45° C. with stirring. After heating, the resulting brown liquid was dialyzed with 1000 MW dialysis tubing for three days at 4° C. to minimize hydrolysis of the t-butyl peroxyester. The pH of the dialysis water was maintained at 7.0 to reduce hydrolysis. The resulting product was lyophilized and analyzed by $^1$H NMR, in DMSO-$d_6$, showing the following peaks: 7.65 ppm, 3.00 ppm, 2.79 ppm, 2.33 ppm, 2.07 ppm, 1.74 ppm, 1.51 ppm, 1.25 ppm, 1.09 ppm, 0.84 ppm, 0.73 ppm. The NMR integrations were approximate due to broad nature of peaks, however, it was possible to note the introduction of alkyl peaks at 1.25 ppm due to new t-butyl moieties as well as 2.33 ppm, 2.07 ppm, and 1.74 ppm from the alkyl backbone of the iodoperester.

II. Synthesis of a PVP:DMAPMA-Peroxyester Polymer

The following procedure was carried out to provide a PVP:DMAPMA polymer having pendent peroxyester groups.

PVP:DMAPMA (0.5007 g) as described in Example 2, III., was dissolved in 8.5 ml DMSO. To the PVP:DMAPMA solution was added 6-iodohexanoyl t-butyl peroxyester (0.4007 g; 1.28 mmole).

The reaction mixture was heated overnight at 45° C. with stirring. After heating, the resulting brown liquid was dialyzed with 1000 MW dialysis tubing for three days at 4° C. to minimize hydrolysis of the t-butyl peroxyester. The pH of the dialysis water was maintained at 7.0 to also reduce hydrolysis. The resulting product, a brown oil with a yield of 0.54 g, was lyophilized and analyzed by $^1$H NMR, in DMSO-$d_6$, showing the following peaks: 7.3 ppm, 3.1 ppm, 2.0 ppm, 1.8 ppm, 1.6 ppm, 1.5 ppm, 1.25 ppm, 0.8 ppm, The NMR integrations were approximate due to broad nature of peaks, however, it was possible to note the introduction of alkyl peaks at 1.25 ppm due to new t-butyl moieties.

EXAMPLE 4

Peroxyester and Peroxyester-Coupled Polymer Compounds form Radical Species Upon Heating Thermal reactivities and radical formation following thermal decomposition of the 6-iodohexanoyl t-butyl peroxyester compound, as described in Example 1, and the DMA:APMA-peroxyester polymer, as described in Example 3, were demonstrated. Two different methods were used to demonstrate thermal reactivity. In one, formation of a hydrogen-abstracting and a coupling radical species following thermal decomposition of peroxyester and peroxyester-polymer compounds was shown by NMR analysis. In another, the formation of radical species following decomposition of the peroxyester polymer was demonstrated using a radical recombination assay.

I. NMR Analysis of Thermal Decomposition

6-Iodohexanoyl t-butyl peroxyester was dissolved in DMSO. The solution was heated to 80° C. and NMR peaks at 1.27 ppm (corresponding to the t-butyl peroxyester) and at 1.13 ppm (corresponding to the t-butanol) over a period of 60 minutes. Upon heating to 80° C. it was found that the peroxyester and the peroxyester polymer readily decomposed due to oxygen-oxygen bond scission. Appearance of the t-butanol species peaked after 20 minutes.

II. Radical Recombination Assay

The compound DPPH (2,2-diphenyl-1-picrylhydrazyl radical) is useful for determining radical content as it can combine with another radical in solution, resulting in a reduction in absorbance at 515 nm. In this example, this reaction was used to quantify peroxyester content in solution.

Mixtures were prepared by adding one ml of a 0.1 mM solution of DPPH in dodecane to 200 µL of solutions of 0.5 mg/ml DMA:APMA peroxyester polymer having 10%, 20%, or 30% molar peroxyester coupling (as described in Example 3) in deionized water. A control solution contained DPPH without any polymer, which had an $A_{515}$~1.0. The solutions were sparged for 30 seconds, then sealed and placed overnight at 70° C., with vigorous stirring to ensure mixing between the solutions. The absorbance of the solutions at 515 nm was taken and moles of DPPH radical consumed were calculated, which provided a value for the moles peroxyester/gram polymer. Results are shown in Table 1.

Peroxyester polymers having a higher percentage of molar peroxyester derivatization showed a greater reduction in absorbance at 515 nm. Table 1 also shows that the theoretical peroxyester content on the polymer was generally in agreement with the peroxyester content on the polymer as calculated using the DPPH assay.

TABLE 1

| Sample | Absorbance at 515 nm | Theoretical moles peroxyester/ gram polymer | Actual moles peroxyester/ gram polymer |
|---|---|---|---|
| Control, no polymer | 0.956 | — | — |
| 10% peroxyester polymer | 0.931 | $3.9 \times 10^{-4}$ | $3.6 \times 10^{-4}$ |
| 20% peroxyester polymer | 0.910 | $7.8 \times 10^{-4}$ | $6.7 \times 10^{-4}$ |

TABLE 1-continued

| Sample | Absorbance at 515 nm | Theoretical moles peroxyester/ gram polymer | Actual moles peroxyester/ gram polymer |
|---|---|---|---|
| 30% peroxyester polymer | 0.785 | $1.2 \times 10^{-3}$ | $2.5 \times 10^{-3}$ |

EXAMPLE 5

Preparation of Peroxyester Polymer-Coated Plastic Substrates

In this example, DMA:APMA-peroxyester polymers, as described in Example 3, were thermally coupled to plastic substrates.

Polyvinylchloride (PVC), polystyrene (PS), and polyurethane (PU) substrate of an approximate size of 2 cm×2 cm (obtained from PS-Goex Plastics, Janesville, Wis.; PVC-VWR, Westchester, Pa.; PU-Medical Profiles, Inc., Livonia, Mich.). Substrates were cleaned by rinsing twice with isopropanol. The cleaned PVC, PS, and PU substrates were then hand-dipped into solutions of the DMA:APMA-peroxyester polymers (at concentrations ranging from 5-30%) in isopropanol, wherein the polymer concentration ranging from 0.01 mg/ml to 10 mg/ml. Of the conditions tested, it was determined that a very good coating was produced by dipping the substrate twice in 1 mg/ml polymer solutions in isopropanol and allowing the piece to completely air dry between coatings.

The air-dried pieces were heated between 1 and 15 hrs at 80° C., followed by two cycles of rinsing in deionized water for 30 minutes each at room temperature on a shaker to remove unbound polymer.

PVC, PS, and PU were all able to serve as substrates for peroxyester-polymer coupling. It was estimated that the polymer was coupled to the PVC, PS, and PU substrates after 1 hour at 80° C., although longer incubation increased polymer coupling.

EXAMPLE 6

Peroxyester Polymer-Coated Plastic Substrates Demonstrate Increased Lubricity

Various types of coated plastic surfaces were analyzed for improved wettability by measuring their static contact angle with water. Peroxyester polymer-coated substrates showed improved wettability, even after the surface of the substrate was physically challenged by performing a rub procedure.

I. In order to determine the effect peroxyester polymer coating on wettability, PS substrates were first contacted with unquenched and quenched (control) peroxyester DMA-APMA polymers having either 5% or 10% peroxyester content and heated according to the procedure detailed in Example 5. Quenched peroxyester DMA-APMA polymers were prepared by heating the peroxyester polymer in isopropanol, the radicals generated being quenched by reaction with isopropanol prior to contacting the substrate, creating carboxylic acid or alkane functionalities in place of the peroxyester groups. The coated and uncoated PS substrates were rinsed multiple times to remove any unbound polymer.

Drops of water were applied to the coated and uncoated PS substrates and static contact angles were measured with a Kruess DSA 10 gongiometer (Kruess GmbH, Hamburg, Germany) using automated circle fitting algorithms. At least three drops of 3 µl each per sample were averaged.

Contact angle measurements for the PS-coated substrates and controls are shown in Table 2. A lower contact angle correlates with improved wettability. The results show that the greatest reduction in contact angle was achieved when unquenched (fresh) peroxyester was used to coat the PS surface.

TABLE 2

| Sample | Contact Angle (°) |
|---|---|
| Uncoated polystyrene | 80.3 ± 1.3 |
| 5% peroxyester, quenched overnight | 79.3 ± 1.5 |
| 5% peroxyester, fresh solution | 32.6 ± 2.0 |
| 10% peroxyester, quenched overnight | 48.5 ± 16.3 (range: 33-76) |
| 10% peroxyester, fresh solution | 30.7 ± 0.9 |

II. Contact angle measurements and durability of the coated substrates were also tested for the coated PS substrates. The durability of the peroxyester-polymer coating was tested by rubbing the surface of the coated substrate multiple times and then performing contact angle measurements.

PS substrates were first contacted with solutions containing DMA-APMA peroxyester polymers at 5 mg/ml, having either 5% or 10% peroxyester content, and treated by heating for either 1 hour or overnight. Unheated substrates in contact with the peroxyester polymer solutions were used as a control. PS substrates were then dried and wiped five times with a lint-free cloth. This wiping procedure was performed to simulate abrasive conditions a medical device experiences within a body.

Contact angle measurements are shown in Table 3. The results show that, generally, heating the PS substrates with the peroxyester polymer overnight resulted in better wettability and lubricity as indicated by the low contact angle measurements. After wiping multiple times the PS substrates coated with the peroxyester polymer overnight still provided a contact angle that was significantly lower that the PS substrates that were heated for one hour. Results are shown in Table 3.

TABLE 3

| Sample | Contact Angle (°) after rinsing | Contact Angle (°) after 5x Rub |
|---|---|---|
| Uncoated Polystyrene | 83.0 ± 1.6 | — |
| 5% peroxyester unheated | 81.1 ± 2.2 | — |
| 5% peroxyester heated 1 hr | 71.5 ± 3.7 | 73.5 ± 5.9 |
| 5% peroxyester heated overnight | 37.5 ± 1.7 | 60.0 ± 1.4 |
| 10% peroxyester unheated | 80.7 ± 3.1 | — |
| 10% peroxyester heated 1 hr | 60.7 ± 1.7 | 85.2 ± 2.7 |
| 10% peroxyester heated overnight | 47.2 ± 2.1 | 60.3 ± 3.6 |

III. The peroxyester polymer was shown to coat substrates made of different plastics and also provide these coated substrates with improved wettability and lubricity, as demonstrated by a lower contact angle. DMA-APMA peroxyester polymers a 10% peroxyester content and at concentrations of 0.5 mg/ml and 5.0 mg/ml in isopropanol were coated on PS, PVC, and PU substrates overnight at 80° C. Controls substrates were uncoated. The substrates were washed and the contact angle was measured. Results are shown in Table 4.

TABLE 4

| Sample | Contact Angle |
| --- | --- |
| Uncoated PS | 79.6 ± 4.9 |
| 0.5 mg/ml on PS | 38.5 ± 2.4 |
| 5.0 mg/ml on PS | 49.0 ± 2.1 |
| Uncoated PVC | 85.2 ± 2.7 |
| 0.5 mg/ml on PVC | 68.5 ± 1.3 |
| 5.0 mg/ml on PVC | 70.5 ± 2.6 |
| Uncoated PU | 71.1 ± 2.6 |
| 0.5 mg/ml on PU | 56.1 ± 2.2 |
| 5.0 mg/ml on PU | 58.3 ± 2.3 |

EXAMPLE 7

Peroxyester Polymer-Coated Plastic Substrates Demonstrate Reduced Protein Adsorption The ability of peroxyester polymer coatings to reduce protein adsorption on plastic substrates was tested. The results indicate that a significant reduction of protein adsorption was seen when plastic substrates were coated with the peroxyester polymer coating. Reduction in protein adsorption was demonstrated for three different proteins and on three different plastic materials, indicating that the peroxyester coatings have a broad range of applicability for reducing protein adsorption.

I. Peroxyester polymer-coated PS, PVC, and PU substrates, as prepared in Example 6, section III, were cut into 0.5 cm×1.5 cm pieces and placed individually in test-tubes. As controls uncoated PS, PVC, and PU were used. A solution containing fibrinogen (1 ml of 1 mg/ml dissolved in 1× phosphate buffered saline (PBS)) was added to each test-tube and the tubes were incubated at 37° C. for one hour with rotation at 140 rpm. After incubation, the fibrinogen solution was aspirated off the surfaces and the pieces were washed three times in 2 ml of TRIS-buffered saline with 0.1% Tween-20 (TNT buffer).

After the final wash, 1 ml of 1:10,000 dilution of HRP-labeled goat anti-human fibrinogen antibody (Rockland Immunologicals, Gilbertsville, Pa.) in 1× phosphate buffered saline (PBS) buffer was added to each test tube, and incubated at room temperature for 30 minutes with mixing at 200 rpm. The antibody solution was then aspirated off each piece, and the pieces were rinsed three times in 2 ml of TNT buffer. The rinsed coupons were then transferred to new test tubes and 1 ml of 1:1H$_2$O$_2$/TMB (3,3',5,5' tetramethylbenzidine) solution which colors in the presence of peroxidase. After 15 minutes, 200 µls of each sample solution was transferred to 4 wells of a 96 well microtiter plate and the absorbance was determined at 650 nm using a spectrophotometer (Molecular Devices, SpectraMax 384 Plus, Sunnyvale, Calif.). Results are shown in Table 5.

TABLE 5

| Sample | Fibrinogen Adsorption | % of Uncoated Value |
| --- | --- | --- |
| Uncoated PS | 0.970 | |
| 0.5 mg/ml on PS | 0.316 | 32% |
| 5.0 mg/ml on PS | 0.237 | 24% |
| Uncoated PVC | 0.978 | |

TABLE 5-continued

| Sample | Fibrinogen Adsorption | % of Uncoated Value |
| --- | --- | --- |
| 0.5 mg/ml on PVC | 0.615 | 63% |
| 5.0 mg/ml on PVC | 0.495 | 51% |
| Uncoated PU | 0.686 | |
| 0.5 mg/ml on PU | 0.446 | 65% |
| 5.0 mg/ml on PU | 0.373 | 54% |

II. The peroxyester polymer was also shown to reduce adsorption of different proteins on peroxyester-coated plastic surfaces. PS substrates were first coated with 10% peroxyester-polymer at 5 different concentrations: 0.05 mg/ml, 0.1 mg/ml, 0.5 mg/ml, 1.0 mg/ml, and 5.0 mg/ml according to the procedure in section I of this example. Uncoated PS was used as a control.

The coated- and uncoated-PS substrates were then incubated with three different proteins, human fibrinogen (hFib), bovine serum albumin (BSA), and goat anti-rabbit immunoglobulin (GaR IgG). Incubation of the protein solutions with the PS substrates were performed using the conditions as detailed in Example 5, Section I.

In order to determine fibrinogen, albumin, and immunoglobulin adsorption, HRP-labeled goat anti-human fibrinogen antibody, HRP-labeled rabbit anti-BSA antibody, and HRP-labeled rabbit anti-goat antibody, were incubated with the protein-challenged poly-coated PS substrates, respectively. Antibody incubations were performed and analysis was carried out according to the procedure detailed in Example 5, Section I. Results are shown in Table 6.

TABLE 6

| Sample | IgG | BSA | Fib |
| --- | --- | --- | --- |
| UC PS | 1.082 | 0.889 | 0.615 |
| 0.05 mg/ml | 0.598 | 0.284 | 0.333 |
| 0.1 mg/ml | 0.36 | 0.575 | 0.28 |
| 0.5 mg/ml | 0.263 | 0.325 | 0.265 |
| 1.0 mg/ml | 0.203 | 0.261 | 0.239 |
| 5.0 mg/ml | 0.315 | 0.248 | 0.211 |

EXAMPLE 8

Synthesis of an Acrylamide-Based Polymers Having Pendent Thermally-Reactive Peroxyester Groups and Alkyl Quaternary Amine Groups The halogenated peroxyester compounds, as prepared in Example 1, and halogenated alkyl compounds were attached to amine groups on acrylamide-based copolymers through nucleophilic reactions to create quaternized peroxyester polymers.

The 6-iodohexanoyl t-butyl peroxyester as described in Example 1, II. B., was combined in solution with the AA:D-MAPMA polymer, as described in Example 2, II., and iodoalkyl compounds (iodohexane, iododecane, and iodohexadecane) in order to prepare the quaternized peroxyester polymer. Six different quaternized peroxyester AA:D-MAPMA polymers were prepared, having variations in the peroxyester content, the quaternary amine content, and also variations in the length of the alkyl chains of the quaternized amine group. The variations are summarized in Table 7.

The following procedure was carried out in order to synthesize a quaternized peroxyester polymer having a target 12.5 mole % peroxyester content, 25 mole % quaternary amine content, and having 6-carbon alkyl groups attached to the quaternary amines. AA:DMAPMA polymer (0.5043 g; 2.1 mmole; 50 mole % DMAPMA, approx. 5000 MW) was dissolved in 11 ml DMSO. A solution of 0.1606 g 6-iodohexanoyl t-butyl peroxyester (0.51 mmole) in 2 ml of DMSO was added to the AA:DMAPMA polymer solution, and also 0.15 ml iodohexane (1.0 mmole). The molar concentrations of reagents used for making quaternized peroxyester AA:D-MAPMA polymers is provided in Table 7. The reaction mixtures were heated overnight at 45° C. with stirring. After heating, the resulting brown liquid was dialyzed with 1000 MW dialysis tubing for three days, at 4° C. to minimize hydrolysis of the t-butyl peroxyester.

The resulting product was lyophilized and analyzed by $^1$H NMR: 7.65 ppm (1H), 7.0 ppm (1H), 6.75 ppm (1H), 3.02 ppm (2H), 2.12 ppm (1H), 1.67 ppm (2H), 1.26 ppm (7H), 0.89 ppm (2H), in DMSO-$d_6$. NMR integrations are approximate due to broad nature of peaks, however, the large reduction of the 2.12 ppm peak is likely to be due to quaternization of amino group, which shifts these portions into a region of overlap with water (~3.5 ppm), as well as the introduction of alkyl peaks at 1.26 ppm and 0.89 ppm due to new hexane and t-butyl moieties.

treatment, followed by a soak time of at least 2 hours in fresh deionized water, and then wiped gently to remove excess non-immobilized polymer.

The PVC substrates were then analyzed for lubricity by performing contact angle measurements as described in Example 6, and for polymer coating efficiency and thickness using fluorescein stain assay. The fluorescein stain assay allows for quantitation of quaternary amines, providing a measure of coating efficiency and thickness.

The fluorescein stain assay was performed by dipping the quaternized peroxyester polymer-coated PVC pieces in a 1% w/v aqueous solution of fluorescein sodium salt (Aldrich Chemical, St. Louis, Mo.) for 15 seconds, and then rinsing twice in deionized water for at least 30 seconds. At this point, the orange color of the stain was visible on the coated pieces due to fluorescein bound to the quaternary ammonium groups. The fluorescein was then released from the coating on the PVC by immersing in an aqueous solution of 0.1% w/v cetyltrimethylammonium chloride, which displaces the fluorescein, for at least 30 minutes with shaking. The adsorbance of the fluorescein in the solutions was measured at 502 nm using a Shimadzu UV1601 spectrophotometer in order to

TABLE 7

| Peroxyester % | Alkyl Quat % and chain length | 6-iodohexanoyl t-butyl peroxyester | iodohexane | Iododecane | Iodo-16ane |
|---|---|---|---|---|---|
| 12.5 | 25 6-carbon | 0.51 mmole | 1.0 mmole | | |
| 12.5 | 25 10-carbon | 0.51 mmole | | 1.0 mmole | |
| 12.5 | 25 16-carbon | 0.51 mmole | | | 1.0 mmole |
| 10 | 40 6-carbon | 0.41 mmole | 1.6 mmole | | |
| 10 | 40 16-carbon | 0.41 mmole | | | 1.6 mmole |
| 40 | 10 6-carbon | 1.63 mmole | 0.4 mmole | | |

EXAMPLE 9

Preparation of Quaternized Peroxyester Polymer-Coated Plastic Substrates

In this example, the quaternized peroxyester AA:DMAPMA polymer, as described in Example 8, was thermally coupled to plastic substrates. This example also shows that following thermal-coupling, substrates having a quaternized peroxyester polymer coating demonstrated increased resistance to a physical challenge as measured by a rub test.

I. Pieces of PVC and low density polyethylene (IdPE) were cleaned with isopropanol prior to coating. Two different approaches were taken to coat the substrates. In one, the PVC and LDPE pieces were hand-dipped into solutions containing the quaternized peroxyester polymer at concentrations of 1 and 10 mg/ml in deionized water and air dried. After the PVC and LdPE pieces dried they were heated at 80° C. for 1 to 15 hours.

In another approach PVC and LDPE pieces were also soaked in solutions of quaternized peroxyester polymer at concentrations of 1 and 10 mg/ml and then the solutions containing the substrates were heated at 80° C. for 1 to 15 hours.

In both methods, the coated PVC and LdPE pieces were then washed 5 times with deionized water after the heat determine the amount of staining on the sample pieces. Results of contact angle measurements and fluorescein staining are shown in Table 8.

TABLE 8

| Peroxyester % | Alkyl Quat % and chain length | | Contact Angle (°) | Stain Abs. at 502 nm |
|---|---|---|---|---|
| 12.5 | 25 | 6-carbon | 72.0 ± 9.8 | 0.069 ± 0.022 |
| 12.5 | 25 | 10-carbon | 87.2 ± 4.3 | 0.071 ± 0.003 |
| 12.5 | 25 | 16-carbon | 97.6 ± 5.7 | 0.067 ± 0.004 |
| 10 | 40 | 6-carbon | 73.8 ± 14.4 | 0.050 ± 0.004 |
| 10 | 40 | 16-carbon | 99.4 ± 2.3 | 0.011 ± 0.001 |
| 40 | 10 | 6-carbon | 85.5 ± 5.4 | 0.083 ± 0.021 |
| Uncoated PVC | | — | 89.6 ± 4.0 | 0.001 ± 0.001 |

As illustrated from the data in Table 7 PVC samples coated with quaternized peroxyester polymers having long alkyl chains demonstrated increased contact angle measurements, due to the increased hydrophobicity of the surface provided by the long alkyl chains. Of the polymer coated PVC substrates tested, substrates having coatings with 25% quaternary polymers provided the thickest and most reproducible coatings, based on the flourescence stain assay.

II. Contact angle measurements and durability were also tested on the PVC substrates coated with the quaternized peroxyester polymers that had either been treated with heat or not treated with any heat (control). Pieces of PVC were coated with quaternized peroxyester AA:DMAPMA polymers having 12% peroxyester content, 25% quaternary amine content, and various alkyl chain lengths. Heating was performed overnight at 80° C. As controls, substrates contacted with the same AA:DMAPMA polymers, but not heated, were used. The samples were rinsed in deionized water and then gently wiped with a lint free cloth and then contact angle measurements were performed as described in Example 6, as well as a fluorescence stain assay. Results are shown in Table 9.

TABLE 9

| Peroxyester % | Alkyl Quat % and chain length | | Heating | Contact Angle (°) | Stain Abs. at 502 nm |
|---|---|---|---|---|---|
| 12 | 25 | 6-carbon | Yes | 63.4 ± 15.2 | 0.042 |
| 12 | 25 | 10-carbon | Yes | 78.4 ± 3.5 | 0.019 |
| 12 | 25 | 16-carbon | Yes | 84.6 ± 4.7 | 0.035 |
| 12 | 25 | 6-carbon | No | 88.9 ± 2.8 | 0.012 |
| 12 | 25 | 10-carbon | No | 87.5 ± 3.6 | 0.009 |
| 12 | 25 | 16-carbon | No | 89.1 ± 2.4 | 0.008 |

These results demonstrate that, after physically challenging the surfaces of the substrates by rubbing, the PVC substrates contacted with the quaternized peroxyester polymer and heated overnight resulted in better wettability as compared to the unheated substrates as indicated by the low contact angle measurements. The heated substrates also showed higher absorbances, indicating a better coating efficiency and thickness.

III. Quaternized peroxyester polymers were also tested for their ability to coat substrates having more complex geometries as compared to the flat substrates tested herein. PVC and LdPE tubing (inner diameter=¼ inch, outer diameter ⅜ inch, Aldrich Chemical, St. Louis, Mo.) were immersed in a 5 mg/ml solution of quaternized peroxyester AA:DMAPMA polymer having 25% quaternization/6-carbon alkyl and 12% peroxyester content. The quaternized peroxyester AA:DMAPMA polymer solution was dried and then the tubing pieces were heated at 80° C. for one hour. The tubing pieces were then rinsed with deionized water five times and soaked in fresh deionized water for one hour. The tubing pieces were then cut open and wiped gently to remove excess water. Contact angle measurements were then performed. The results are shown in Table 10.

TABLE 10

| Tubing material | Polymer coating | Contact Angle (°) |
|---|---|---|
| PVC | No | 87.5 |
| PVC | Yes | 63 |
| LdPE | No | 95 |
| LdPE | Yes | 78.5 |

These results show that the peroxyester polymer as described herein can be used to coat substrates having surfaces with complex geometries, such as the inner surface of tubes.

EXAMPLE 10

Anti-Microbial and Anti-Adherence Properties of Quaternized Peroxyester Polymer-Coated Plastic Substrates The quaternized peroxyester polymers used to coat PVC substrates as described in Example 8 were tested for their ability to prevent microbial growth in solution by performing a Minimum Inhibitory Concentration (MIC) assay. The quaternized peroxyester polymer coatings were also tested for their ability to prevent bacterial adherence and growth on the PVC substrates by performing an anti-adherence assay.

The MIC assay was performed by first preparing serial dilutions of the polymers listed in Table 10, the dilutions ranging from 0.5 mg/ml to 8 µg/ml. Serial dilutions were prepared using 200 µl of a 1 mg/ml concentrated aqueous solution. 100 µl of each diluted polymer solution was placed in one well of a 96 well plate. A negative control solution was prepared by adding 100 µl of sterile water to 100 µl of Mueller-Hinton (Difco, Becton Dickinson, Franklin Lakes, N.J.) with 1.5% Alamar blue dye without bacteria. This negative control was added to 3 wells of the 96 well plate. 100 µl of a solution containing 1.5% Alamar blue dye and $5 \times 10^5$ CFU/ml of *Staphlococcus aureus* (ATCC 25923, American Type Culture Collection, Manassas, Va.) was added to each of the 100 µl of serially diluted polymer solutions, as well as to the negative controls. A positive control was prepared by adding 100 µl of the Alamar blue/bacteria solution to 100 µl of sterile water. The 96 well plate was incubated overnight at 37° C. A pink color in a well indicated bacterial growth and a blue color no growth. The MIC was determined by visual inspection of the wells, a blue color being outside the limit of the MIC range. Results of MIC assay are shown in Table 11.

The anti-adherence assay was performed by first growing a bacterial culture of *S. aureus* overnight to early stationary phase in tryptic soy broth (TSB) (Becton Dickinson, Franklin Lakes, N.J.). The culture was washed twice in PBS and then sonicated 30 seconds to break up clumps of bacteria (Vertis Versonic 4 mm probe at 130 watts) without destroying the bacteria. The bacterial concentration was adjusted to approximately $10^4$-$10^5$ CFU/ml in PBS and the number of colony forming units (CFU)/ml in the final suspension was determined by plating on tryptic soy agar (TSA) (Becton Dickinson, Franklin Lakes, N.J.). For adherence assays, pieces of polymer-coated substrates were incubated with 3.5 mls of bacteria culture for 2 hours at 25° C. with gentle shaking. Each piece was then placed into a fresh vial and washed four times, two minutes each wash, with shaking at 250 rpm to remove nonadherent bacteria. This method removed nonadherent bacteria, to further wash the pieces, then the adherent bacteria was removed by the sonication step and then plated. In order to recover the bacteria that had adhered to the substrate surface, sonication was performed. Substrates were placed into a vials containing 5 ml of PBS and sonicated on ice for 1 minute, followed by a 1 minute rest, then 1 additional minute of sonication (Vertis Versonic 4 mm probe at 130 watts). The number of CFU/ml in the sonicate was determined by plating the sonicate on TSA and counting the number of colonies that formed after 18 hours at 37° C. Removal of bacteria from the substrate surface was verified by sonicating the samples a second time.

TABLE 11

| Peroxyester % | Alkyl Quat % and chain length | | MIC in mg/ml |
|---|---|---|---|
| 12.5 | 25 | 6-carbon | 0.125 |
| 12.5 | 25 | 10-carbon | 0.250 |
| 12.5 | 25 | 16-carbon | 0.125 |
| 10 | 40 | 6-carbon | 0.030 |
| 10 | 40 | 16-carbon | 0.250 |
| 40 | 10 | 6-carbon | 0.500 |
| Uncoated PVC | — | | — |

Overall, polymers having a high quaternary ammonium content (40%) and a shorter alkyl chain length (6 carbon)

provided coated surfaces with very good overall anti-microbial and anti-adherence properties.

EXAMPLE 11

Preparation of Polyvinylpyrrolidone-Acrylamide based Peroxyester Polymer-Coated Substrates PVP:DMAPMA In this example, a PVP:DMAPMA-peroxyester polymer, as described in Example 3, II was thermally coupled to plastic and metal substrates.

Substrates used were (a) stainless steel (SS), (304L; Goodfellow Cambridge Ltd., Huntingdon, England), metal flats of an approximate size of 6.5 cm×0.5 cm and (b) polyetherblock co-polyamide (PEBAX) rods of an approximate size of 0.3 cm×10.0 cm O.D. (118, Light Blue, 20% Barium Sulfate, Medical Profiles, Inc., Livonia, Mich.). PEBAX substrates were cleaned by wiping with isopropyl alcohol (IPA). The SS substrates were prepared and treated with silane by the methods as described in Example 1 of U.S. Pat. No. 6,706,408. The cleaned PEBAX, and SS substrates were dipped into a solution of the PVP:DMAPMA-peroxyester polymer in deionized water, wherein the polymer concentration was 20 mg/ml. Dip coating was performed at room temperature as follows. The SS flat or PEBAX rods were dipped into the polymer solution at a rate of 1.0 cm/sec, held in solution for 2 minutes, and then withdrawn from the solution at the rate of 0.10 cm/sec. Following coating with the polymer solution, the PVP:DMAPMA-peroxyester polymer coated SS flats and the PVP:DMAPMA-peroxyester polymer coated PEBAX rods were air-dried for approximately 10 minutes, or until the PVP:DMAPMA-peroxyester polymer coating was dry. The coated SS flats and PEBAX rods were put into an oven set at 110° C. for approximately 16 hours.

After removal from the oven, the coated PEBAX and SS substrates were stained with a 0.35% aqueous solution of Congo Red. Extensive washing of the PEBAX and SS substrates after staining under a flow of tapwater and rubbing the coated surfaces between thumb and forefinger (approximately 30 seconds) indicated a strongly adherent coating.

Based on these results, the PVP:DMAPMA-peroxyester polymer was able to be coupled to the surface of the PEBAX and silane-coated SS substrates upon heating. It was estimated that the polymer was coupled to the PEBAX and SS substrates after 1 hour at 110° C., although longer incubation increased polymer coupling.

EXAMPLE 12

Preparation of Polyvinylpyrrolidone-Acrylamide Peroxyester Polymer Coated Substrates with a Polyvinylpyrrolidone Topcoat In this example, the PVP:DMAPMA-peroxyester polymer, as described in Example 3, II, was thermally coupled to plastic and metal substrates. A coated layer of polyvinylpyrrolidone was applied to the PVP:DMAPMA-peroxyester polymer coated substrate to improve the lubricity of the surface.

The substrates used were SS metal flats and PEBAX rods as described in Example 11. Substrates were cleaned, and prepared as described in Example 11 and coated with the PVP:DMAPMA-peroxyester polymer as described in Example 3. After air drying of the PVP:DMAPMA-peroxyester polymer on the SS or PEBAX substrates, an aqueous solution of 10 mg/ml of polyvinylpyrrrolidone (PVP) (K90F, BASF Corp., Germany) was dipcoated over the PVP:DMAPMA-peroxyester polymer layer. The SS flats or PEBAX rods dipped into the PVP solution at a rate of 1.0 cm/sec, held in solution for 8 seconds, and then withdrawn from the solution at a rate of 1.0 cm/sec. The PVP coating was dried for approximately 10 minutes (or until the coated surface was dry). Next, the coated SS metal flats and coated PEBAX rods were put into an oven set at 110° C. for approximately 16 hours.

After removal from the oven, the coated PEBAX and SS substrates were stained with a 0.35% aqueous solution of Congo Red. After staining, extensive washing of the PEBAX and SS substrates under a flow of tapwater and rubbing the coated surfaces between thumb and forefinger (approximately 30 seconds) indicated a strongly adherent and lubricious coating.

EXAMPLE 13

Preparation of Polyvinylpyrrolidone-Acrylamide Peroxyester Polymer and Polyvinylpyrrolidone Coated Substrates In this example, a plastic substrate having a coating of two layers was prepared. The first layer was PVP:DMAPMA-peroxyester polymer-containing layer and the second layer was a PVP:DMAPMA-peroxyester polymer/PVP-containing layer.

The plastic substrates used were 6.5 cm×0.5 cm PEBAX rods. Substrates were cleaned and coated with a PVP:DMAPMA-peroxyester polymer solution as described in Example 3 (10 mg/ml in 75% IPA/25% deionized water). The PEBAX rods were dipped into the PVP:DMAPMA-peroxyester polymer solution at a rate of 1.0 cm/sec, held in solution for 60 seconds, and then withdrawn from the solution at a rate of 1.0 cm/sec. The PEBAX rods having this first coated layer were then air-dried as previously described and incubated in an oven at 110° C. for approximately 16 hours to couple the polymer to the surface. For the second coat, a coating solution consisting of PVP (at 7.5 mg/ml) and PVP:DMAPMA-peroxyester polymer (at 15 mg/ml) in 75% IPA was prepared. The previously coated and heat-treated PEBAX rods were dipped into this PVP:DMAPMA—peroxyester polymer/PVP solution and using the dipcoating parameters as described for the first coat. After air drying of the second coat, the coated PEBAX rods were returned to 110° C. oven for approximately 5 hours.

After removal from the oven, the PEBAX rod was stained with a 0.35% aqueous solution of Congo Red. After staining, extensive washing of the PEBAX rod under a flow of tapwater and rubbing the coated surfaces between thumb and forefinger (approximately 30 seconds) indicated a strongly adherent and lubricious coating.

What is claimed is:

1. A method for forming a coating comprising steps of:
    a) providing a polymer comprising
        i) a backbone comprising thermally-stable linkages and
        ii) a thermally-reactive group pendent from the backbone;
    b) disposing the polymer on all or a portion of a surface of an article; and
    c) heating the polymer, wherein thermally-reactive group homolytically cleaves upon heating resulting in the generation of radical species comprising a second radical species and a polymer-coupled radical species, wherein the second radical species is more reactive than the polymer-coupled radical species, and wherein the polymer-coupled radical species that forms covalent bonds with a target moiety and becomes associated with the surface of the article, thereby forming the coating.

2. The method of claim 1 wherein the thermally-reactive group comprises a peroxide group.

3. The method of claim 2 wherein the thermally-reactive group comprises a peroxyester group.

4. The method of claim 1 wherein the polymer coupled radical species comprises an

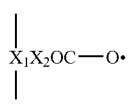

(alkyldioxyl) radical species,
wherein $X_1$ is a portion of the polymeric backbone of the polymer, and $X_2$ is selected from the group consisting of alkyl, benzyl, diphenylacetyl, phenylacetyl, benzoyl, phenylbenzyl, hydrocinnamoyl, mandelyl, phenacyl, phenethyl, thiophenacyl, triphenylmethyl, biphenylacetyl, biphenylethyl, biphenylmethyl, allyl, and substituted allyl.

5. The method of claim 1 wherein the thermally-reactive group has a decomposition temperature of 110° C. or less.

6. The method of claim 1 which provides the formation of a hydrophilic coating.

7. The method of claim 1 wherein the backbone is selected from the group consisting of polyester, polycarbonate, polyamide, polyether, polysulfone, polyurethane, and polyimide backbones.

8. The method of claim 1 wherein the backbone is formed from monomeric units having ethylenically unsaturated groups.

9. The method of claim 1 wherein the backbone comprises (meth)acrylamide, acrylamide, or vinylpyrrolidone monomeric units.

10. The method of claim 9 wherein the backbone comprises acrylamide.

11. The method of claim 1 wherein the polymer has a molecular weight of 1000 Da or greater.

12. The method of claim 11 wherein the polymer has a molecular weight of 5000 Da or greater.

13. The method of claim 1 wherein the polymer comprises 10 molar percent or more thermally-reactive groups.

14. The method of claim 1 wherein the polymer further comprises pendent quaternary amine groups.

15. The method of claim 14 wherein the polymer comprises 10 molar percent or more pendent quaternary amine groups.

16. The method of claim 1, wherein the polymer does not include an ethylenically unsaturated group.

17. The method of claim 1 wherein (c) the polymer becomes covalently bonded to the surface.

18. The method of claim 1 wherein step (b) the polymer is disposed on an article comprising one or more additional coated layer(s).

19. The method of claim 18 wherein step (c) the polymer becomes covalently bonded to a second polymer present in the one or more additional coated layer(s).

20. The method of claim 19 wherein the second polymer comprises poly(vinyl)pyrrolidone.

21. The method of claim 1 wherein the article comprises a complex geometry.

22. The method of claim 1 wherein step (b), step (c), or both steps (b) and (c), further includes drying the polymer on the surface of the substrate.

23. The method of claim 1 wherein heating is performed at a temperature of not more than 200° C.

24. The method of claim 23 wherein heating is performed at a temperature in the range of 40° C. to 80° C.

25. The method of claim 1 wherein the polymer is disposed on the article at a concentration of 0.5 mg/ml or greater.

26. The method of claim 1 wherein the backbone is selected from polyvinyl polymers.

27. The method of claim 26 wherein the backbone is selected from the group consisting of poly(meth)acrylamides, polyacrylamides, and poly(vinylpyrrolidone).

28. The method of claim 1 wherein the article comprises an inner surface and in step (b) the polymer is disposed on the inner surface of the article.

29. The method of claim 28 wherein the article is selected from the group of consisting of stents and catheters.

30. A method for coating an article comprising steps of:
a) providing a polymer comprising
  i) a backbone comprising thermally-stable linkages and
  ii) a thermally-reactive group pendent from the backbone comprising a pair of atoms with a heat sensitive labile bond selected from the group consisting of oxygen-oxygen, nitrogen-oxygen, and nitrogen-nitrogen;
b) disposing the polymer on all or a portion of a surface of the article; and
c) heating the polymer, wherein thermally-reactive grow homolytically cleaves upon heating resulting in the generation of radical species comprising a second radical species and a polymer-coupled radical species, wherein the second radical species is more reactive than the polymer-coupled radical species, and wherein the polymer-coupled radical species that forms covalent bonds with a target moiety and becomes associated with the surface of the article, thereby forming the coating.

31. A method for coating an article comprising steps of
a) providing a polymer comprising
  i) a backbone comprising thermally-stable linkages and
  ii) a thermally-reactive peroxyester group pendent from the backbone;
b) disposing the polymer on all or a portion of a surface of the article; and
c) heating the polymer, wherein thermally-reactive group homolytically cleaves upon heating resulting in the generation of radical species comprising a second radical species and a polymer-coupled radical species, wherein the second radical species is more reactive than the polymer-coupled radical species, and wherein the polymer-coupled radical species that forms covalent bonds with a target moiety and becomes associated with the surface of the article, thereby forming the coating.

32. A method for coating an inner surface of a medical article comprising steps of:
a) providing a polymer comprising
  i) a backbone comprising thermally-stable linkages and
  ii) a thermally-reactive group pendent from the backbone;
b) disposing the polymer on all or a portion of the inner surface of the medical article; and
c) heating the polymer, wherein thermally-reactive group homolytically cleaves upon heating resulting in the generation of radical species comprising a second radical species and a polymer-coupled radical species, wherein the second radical species is more reactive than the polymer-coupled radical species, and wherein the to form a polymer-coupled radical species forms covalent bonds with a target moiety and becomes associated with the inner surface of the article, thereby forming the coating.

33. The method of claim 1 wherein the polymer coupled radical species comprises an alkyl group pendent from the backbone of the polymer.

34. The method of claim 1 wherein the polymer coupled radical species comprises a chemical group selected from the group consisting of benzyl, diphenylacetyl, phenylacetyl, benzoyl, phenylbenzyl, hydrocinnamoyl, mandelyl, phenacyl, phenethyl, thiophenacyl, triphenylmethyl, biphenylacetal, biphenylethyl, biphenylmethyl, allyl, substituted allyl, and carboxyl, wherein the chemical group is pendent from the backbone of the polymer.

35. The method of claim 1, wherein step (b) the polymer is present in a coating composition at a concentration of 0.5 mg/mL or greater, and the coating composition is disposed on the on all or a portion of the surface of the article.

36. The method of claim 35, wherein the polymer is present in the coating composition at a concentration in the range of 0.5 mg/mL to 10 mg/mL.

37. The method of claim 1 wherein the second radical species comprises an .OR (alkoxy) radical species.

38. The method of claim 1, wherein the polymer is formed by a process comprising nucleophilic reaction of a pre-polymer comprising thermally stable linkages with a compound comprising a thermally-reactive group.

39. The method of claim 38 wherein the process comprising nucleophilic reaction, the compound comprising a thermally-reactive group further comprises a halogen atom.

40. The method of claim 38 wherein the process comprising nucleophilic reaction, the pre-polymer comprises thermally stable linkages and a pendent amine group.

41. The method of claim 38 wherein the nucleophilic reaction comprises iodo-amine coupling.

* * * * *

UNITED STATES PATENT AND TRADEMARK OFFICE
CERTIFICATE OF CORRECTION

| | | |
|---|---|---|
| PATENT NO. | : 7,807,750 B2 | Page 1 of 1 |
| APPLICATION NO. | : 10/944384 | |
| DATED | : October 5, 2010 | |
| INVENTOR(S) | : Kristin S. Taton and Patrick E. Guire | |

It is certified that error appears in the above-identified patent and that said Letters Patent is hereby corrected as shown below:

Column 41,
Line 1 Claim 1, "species that forms" should be --species forms--

Column 42,
Line 35 Claim 30, "species that forms" should be --species forms--

Column 42,
Line 51 Claim 31, "species that forms" should be --species forms--

Column 42,
Line 67 Claim 32, "the to form a ploymer-coupled" should be --the polymer-coupled--

Signed and Sealed this
Seventeenth Day of April, 2012

David J. Kappos
*Director of the United States Patent and Trademark Office*